US010577412B2

(12) United States Patent
Fendel et al.

(10) Patent No.: US 10,577,412 B2
(45) Date of Patent: Mar. 3, 2020

(54) ANTI-PLASMODIUM PARASITE ANTIBODIES

(71) Applicant: Fraunhofer-Gesellschaft zur Foerderung der angewandten Forschung e.V., Munich (DE)

(72) Inventors: Rolf Fendel, Tuebingen (DE); Stefan Barth, Cape Town (ZA); Rainer Fischer, Aachen (DE); Andreas Reimann, Krefeld (DE); Dominika Maskus, Cologne (DE); Torsten Klockenbring, Bonn (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 40 days.

(21) Appl. No.: 15/566,176

(22) PCT Filed: Apr. 11, 2016

(86) PCT No.: PCT/EP2016/057873
§ 371 (c)(1),
(2) Date: Oct. 12, 2017

(87) PCT Pub. No.: WO2016/166040
PCT Pub. Date: Oct. 20, 2016

(65) Prior Publication Data
US 2018/0086823 A1  Mar. 29, 2018

(30) Foreign Application Priority Data
Apr. 12, 2015  (EP) .................. 15163297.3

(51) Int. Cl.
*C07K 16/20* (2006.01)
*A61K 39/00* (2006.01)

(52) U.S. Cl.
CPC ...... *C07K 16/205* (2013.01); *A61K 2039/507* (2013.01); *C07K 2317/14* (2013.01); *C07K 2317/21* (2013.01); *C07K 2317/56* (2013.01); *C07K 2317/565* (2013.01); *C07K 2317/73* (2013.01); *C07K 2317/76* (2013.01); *C07K 2317/92* (2013.01); *Y02A 50/58* (2018.01)

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Wilhelmus et al. |
| 3,850,578 A | 11/1974 | McConnell |
| 3,850,752 A | 11/1974 | Wilhelmus et al. |
| 3,853,987 A | 12/1974 | Dreyer |
| 3,867,517 A | 2/1975 | Ling |
| 3,879,262 A | 4/1975 | Wilhelmus et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,666,828 A | 5/1987 | Gusella |
| 4,683,202 A | 7/1987 | Mullis |
| 4,801,531 A | 1/1989 | Frossard |
| 4,816,397 A | 3/1989 | Boss et al. |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 9,611,318 B2 | 4/2017 | Fendel et al. |
| 10,131,697 B2 | 11/2018 | Boes et al. |
| 10,183,066 B2 | 1/2019 | Boes et al. |
| 10,213,501 B2 | 2/2019 | Spiegel et al. |
| 10,344,082 B2 | 7/2019 | Fendel et al. |
| 2004/0091971 A1 | 5/2004 | Kocken et al. |
| 2004/0175392 A1 | 9/2004 | Pluschke et al. |
| 2005/0031592 A1 | 2/2005 | Doolan |

(Continued)

FOREIGN PATENT DOCUMENTS

| CA | 1340741 C | 9/1999 |
| CN | 102559613 A | 7/2012 |

(Continued)

OTHER PUBLICATIONS

Accession No. BP423581, Dec. 18, 2010.*
Kussie et al, The Journal of Immunology, 152:146-152, 1994.*
Chen et al, The Embo Journal 14(12):2784-94, 1995.*
Bendig (Methods: A Companion to Methods in Enzymology 1995; 8:83-93).*
Mugyenyi et al. "Antibodies to Polymorphic Invasion-Inhibitory and Non-Inhibitory Epitopes of Plasmodium falciparum Apical Membrane Antigen 1 in Human Malaria," Plos One, Jul. 2013, 8(7):e68304.

(Continued)

*Primary Examiner* — Patricia Duffy
(74) *Attorney, Agent, or Firm* — Wagenknecht IP Law Group PC

(57) ABSTRACT

The technology provided herein relates to novel human antibodies against *Plasmodium* parasites, in particular against the malaria parasite *Plasmodium falciparum*. The present disclosure pertains to antibodies against apical membrane antigen 1 (AMA-1). These antibodies have high affinity e.g. to *Plasmodium falciparum* schizonts and merozoites, inhibit the reinvasion of merozoites into erythrocytes and thereby neutralize parasitic multiplication.

12 Claims, 9 Drawing Sheets
Specification includes a Sequence Listing.

(56) References Cited

U.S. PATENT DOCUMENTS

| | | |
|---|---|---|
| 2005/0208020 A1 | 9/2005 | Doolan |
| 2008/0107656 A1 | 5/2008 | Crab |
| 2011/0243982 A1 | 9/2011 | Bruns |
| 2013/0216570 A1 | 8/2013 | Schneerson et al. |
| 2015/0191518 A1 | 7/2015 | Pradel et al. |
| 2018/0311326 A1 | 11/2018 | Edgue et al. |

FOREIGN PATENT DOCUMENTS

| | | |
|---|---|---|
| DE | 102012013860 A1 | 1/2014 |
| EP | 2692357 A1 | 2/2014 |
| EP | 2796147 A1 | 10/2014 |
| JP | 2006-504438 A | 9/2006 |
| WO | 1993004696 A1 | 3/1993 |
| WO | 1993011161 A1 | 6/1993 |
| WO | 1995019011 A2 | 7/1995 |
| WO | 2006/020706 * | 2/2006 |
| WO | 2006/037807 A2 | 4/2006 |
| WO | 2007027860 A2 | 3/2007 |
| WO | 2007041216 A2 | 4/2007 |
| WO | 2008011157 A2 | 1/2008 |
| WO | 2010037063 A2 | 9/2009 |
| WO | 2011100508 A2 | 8/2011 |
| WO | 2012/047679 A2 | 4/2012 |
| WO | 2015144874 A1 | 10/2015 |

OTHER PUBLICATIONS

Coley et al. "Rapid and precise epitope mapping of monoclonal antibodies against Plasmodium falciparum AMA1 by combined phage display of fragments and random peptides," Protein Engineering, 2001, 14(9):691-698.

Coley et al. "The Most Polymorphic Residue on Plasmodium falciparum Apical Membrane Antigen 1 Determines Binding of an Invasion-Inhibitory Antibody," Infection and Immunity, May 2006, 74(5):2628-2636.

Dutta et al. "Overcoming Antigenic Diversity by Enhancing the Immunogenicity of Conserved Epitopes on the Malaria Vaccine Candidate Apical Membrane Antigen-1," PLOS Pathogens, Dec. 2013, 9(12):e1003840.

Miura et al. "Anti-Apical-Membrane-Antigen-1 Antibody Is More Effective than Anti-42-Kilodalton-Merozoite-Surface-Protein-1 Antibody in Inhibiting Plasmodium falciparum Growth, as Determined by the In Vitro Growth Inhibition Assay," Clinical and Vaccine Immunology, Jul. 2009, 16(7): 963-968.

PCT/EP2016/057873 International Search Report dated May 30, 2016.

Jones et al. "A Plant-Produced Pfs25 VLP Malaria Vaccine Candidate Induces Persistent Transmission Blocking Antibodies against Plasmodium falciparum in Immunized Mice," Plos One, 2013, 8(11)e79538(1-10).

Kariu et al. "CelTOS, a novel malarial protein that mediates transmission to mosquito and vertebrate hosts." Molecular Microbiology, Mar. 20, 2006, 59(5):1369-1379.

Kariuki et al. "Plasmodium Falciparum: Purification of the Various Gametocyte Developmental Stages from In Vitro-Cultivated Parasites," The American Society of Tropical Medicine and Hygiene, 1998, 59(4)505-508.

Kaslow et al. "A Vaccine Candidate from the Sexual Stage of Human Malaria that Contains EGF-Like Domains," Nature, 1988, 333(6168)74-76.

Kipriyanov et al. "Recombinant Single Chain Fv Fragments Carrying C-Terminal Cysteine Residues: Production of Bivalent and Biotinylated Miniantibodies." Molecular Immunology, 1994, 31(14):1047-1058.

Kipriyanov et al. "Single-Chain Antibody Streptavidin Fusions: Tetrameric Bifunctional scFv-complexes with Biotin Binding Activity and Enhanced Affinity to Antigen." Human Antibodies Hybridomas, 1995, 6(3):93-101.

Knust et al. "EGF Homologous Sequences Encoded in the Genome of Drosophila melanogaster, and their Relation to Neurogenic Genes," The EMBO Journal, 1987, 6(3)761-766.

Kumar et al. "A Multilateral Effort to Develop DNA Vaccines Against Falciparum Malaria." Trends in Parasitology, Mar. 1, 2002, 18(3):129-135, Elsevier Current Trends, GB.

Kumar et al. "Potent Malaria Transmission-Blocking Antibody Responses Elicited by Plasmodium falciparum Pfs25 Expressed in Escherichia coli after Successful Protein Refolding," Infection and Immunity, Apr. 1, 2014, 82(4)1453-1459.

Kurosawa et al. "A 10-kDa Cyanogen Bromide Fragment from the Epidermal Growth Factor Homology Domain of Rabbit Thrombomodulin Contains the Primary Thrombin Binding Site," The Journal of Biological Chemistry, 1988, 263(13)5993-5996.

Kusi et al. "Immunization with Different PfAMA1 Alleles in Sequence Induces Clonal Imprint Humoral Responses that are Similar to Responses Induced by the Same Alleles as a Vaccine Cocktail in Rabbits," Malaria Journal, 2011, 10(40)1-11.

Lazar et al. "Transforming Growth Factor beta: Mutation of Aspartic Acid 47 and Leucine 48 Results in Different Bological Activities," Molecular and Cellular Biology, Mar. 1988, 8(3):1247-1252.

MacCallum et al."Antibody-antigen Interactions: Contact Analysis and Binding Site Topography," Journal of Molecular Biology, 1996, 262:732-745.

Mahajan et al. "Multiple Antigen Peptide Vaccines against Plasmodium Falciparum Malaria." Infection and Immunity, Nov. 1, 2010, 78(11):4613-4624.

Malker et al. "Parasite Lactate Dehydrogenase as an Assay for Plasmodium Falciparum Drug Sensitivity," The American Journal of Tropical Medicine and Hygiene, 1993, 48(6)739-741.

Marshall et al. "A Second Merozoite Surface Protein (MSP-4) of Plasmodium Falciparum that Contains an Epidermal Growth Factor-Like Domain," Infection and Immunity, 1997, 65(11)4460-4467.

Marshall et al. "Close Linkage of Three Merozoite Surface Protein Genes on Chromosome 2 of Plasmodium Falciparum," Molecular & Biochemical Parasitology, 1998, 94(1)13-25.

Mavoungou et al. "A Duffy Binding-Like Domain Is Involved in the NKp30-Mediated Recognition of Plasmodium falciparum-Parasitized Erythrocytes by Natural Killer Cells," The Journal of Infectious Diseases, 2007, 195:1521-1531.

McCafferty et al. "Phage Antibodies: Filamentious Phage Displaying Antibody Variable Domains" Nature, 1990, 348:552-554.

McCormick et al. "Sporozoite Invasion Assay," Methods in Malaria Research, 5th Edition, Moll et al., Eds, 2008, MR4/ATCC Manassas, Virginia. BioMalPar Paris, France, pp. 138-140.

Mikayama et al. "Molecular Cloning and Functional Expression of a cDNA Encoding Glycosylation-Inhibiting Factor," Procedures of National Academy of Sciences, USA, Nov. 1993, 90:10056-10060.

Ockenhouse et al. "Phase I/Iia Safety, Immunogenicity, and Efficacy Trial of NYVAC-Pf7, a Pox-Vectored, Multiantigen, Multistage Vaccine Candidate from Plasmodium Falciparum Malaria," Journal of Infectious Disease, 1998, 177:1664-1673.

Pachebat et al. "The 22 kDa Component of the Protein Complex on the Surface of Plasmodium Falciparum Merozoites is Derived from a Larger Precursor, Merozoite Surface Protein 7," Molecular & Biochemical Parasitology, 2001, 117:83-89.

Pascalis et al, "Grafting of 'Abbreviated' Complementarity-Determining Regions Containing Specificty-Determining Residues Essential for Ligand Contact to Engineer a Less Immunogenic Humanized Monoclonal Antibody," The Journal of Immunology, 2002, 169:3076-3084.

Patarroyo et al. "A Synthetic Vaccine Protects Humans Against Challenge with Asexual Blood Stages of Plasmodium Falciparum Malaria," Nature, 1988, 332(6160)158-161.

Pearson et al. "An Introduction to Sequence Similarly ("Homology") Searching," Current Protocols Bioinformatics, Author Manuscript; available in PMC 2014, Jun. 2001, pp. 1-9.

PfGAP50 translated Sequence using NCB1 reference sequence NC_0043301.1 PfGAP50 sequence abailable Jul. 29, 2010 translated with ExPASy tool at web.expasy.org/translate/ 3 pages.

Plassmeyer et al. "Structure of the Plasmodium Falciparum Circumsporozoite Protein, A Leading Malaria Vaccine Candidate." The Journal of Biological Chemistry, 2009, 284(39)26951-26963.

(56) References Cited

OTHER PUBLICATIONS

Polley et al. "Human Antibodies to Recombinant Protein Constructs of Plasmodium Falciparum Apical Membrane Antigen 1 (AMA1) and their Associations with Protection from Malaria." Vaccine, 2004, 23:718-728.
Poljak, Roberto J., "Production and Structure of Diabodies." Structure, Dec. 15, 1994, 2:1121-1123.
Pradel et al. "Malaria Sporozoites Actively Enter and Pass Through Rat Kupffer Cells Prior to Hepatocyte Invasion," Hepatology, 2001, 33(5)1154-1165.
Pradel et al. "A Multidomain Adhesion Protein Family Expressed in Plasmodium Falciparum is Essential for Transmission to the Mosquito," The Journal of Experimental Medicine, 2004, 199(11)1533-1544.
Puentes et al. "Identifying Plasmodium falciparum merozoite surface protein-10 human erythrocyte specific binding regions." Biochmie, May 1, 2005, 87(5): 461-472, Masson, Paris, FR.
Rao et al. "Plant Cell Cultures: Chemical Factories of Secondary Metabolites." Biotechnology Advances 2002, 20(2)101-153.
Rathore et al. "Molecular Mechanism of Host Specificity in Plasmodium Falciparum Infection: Role of Circumsporozoite Protein," The Journal of Biological Chemistry, 2003, 278(42)40905-40910.
Bees et al. "The Role of Beta-Hydroxyaspartate and Adjacent Carboxylate Residues in the First EGF Domain of Human Factor IX," The EMBO Journal, 1988, 7(7)2053-2061.
Reese-Channer, Roxanne Rhiannon, "Motorizing Merozites: The Role of Gliding-Associated Proteins GAP45 and GAP50 in Erythrocytic Invasion" Disseratations Publishings, 2007.
Reiling et al. "Evidence that the Erythrocyte Invasion Ligand PhRh2 is a Target of Protective Immunity Against Plasmodium Falciparum Malaria," Journal of Immunology, 2010, 185:6157-6167.
Remarque et al. "A Diversity-Covering Approach to Immunization with Plasmodium Falciparum Apical Membrane Antigen 1 Induces Broader Allelic Recognition and Growth Inhibition Responses in Rabbits," Infection and Immunity, Jun. 2008, 76(6):2660-2670.
Richards et al. "The Future for Blood-Stage Vaccines Against Malaria," Immunology and Cell Biology, 2009, 87(5)377-390.
Richie et al. "Progress and Challenges for Malaria Vaccines," Nature, 2002, 415:694-701.
Roestenberg et al. "Safety and Immunogenicity of a Recombinant Plasmodium Falciparum AMA1 Malaria Vaccine Adjuvanted with Alhydrogel, Montanide ISA 720 or AS02," PloS one, 2008, 3(12)e3960.
Rothberg et al. "Slit: an EGF-Homologous Locus of D. Melanogaster Involved in the Development of the Embryonic Central Nervous System," Cell, 1988, 55(6)1047-1059.
Rudikoff et al. "Single Amino Acid Substitution Altering Antigen-Binding Specificity" Procedures of National Academy of Sciences, USA, Mar. 1982, 79:1979-1983.
Rudinger, J. "Characteristics of the Amino Acids as Components of a Peptide Hormone Sequence," Peptide Hormones, Biology Council, Jun. 1976, pp. 5-7.
Sack et al. "Functional Analysis of the Broadly Neutralizing Human Anti-HIV-1 Antibody 2F5 Produced in Transgenic BY-2 Suspension Cultures," The FASEB Journal, 2007, 21(8)1655-1664.
Schwartz et al. "Atlas of Protein Sequence and Structure," 1978, National Biomedical Research, 5(Supp 3)353-358.
Schwartz et al. "A Review of Malaria Vaccine Clinical Projects Based on the WHO Rainbow Table." Malaria Journal, Jan. 9, 2012, 11(1): 5-8, 11.
Simon et al. "Malaria Parasites Co-opt Human Factor H to Prevent Complement-Mediated Lysis in the Mosquito Midgut" Cell Host & Microbe, Jan. 16, 2013, 13:29-41, Elsevier, Inc.
Simon et al. "Malaria Parasites Co-opt Human Factor H to Prevent Complement-Mediated Lysis in the Mosquito Midgut (Supplementary Information)." Cell Host & Microbe, Jan. 16, 2013, 13:29-41, Elsevier, Inc.
Smith et al. "Comparison of Biosequences," Advances in Applied Mathematics, 1981, 2:482-489.

Srinivasan et al. "Binding of Plasmodium Merozoite Proteins RON2 and AMA1 Triggers Commitment to Invasion," Proceedings of the National Academy of Sciences of the United States of America, 2011, 108(32):13275-13280.
Srinivasan et al. "Immunization with a Functional Protein Complex Required for Erythrocyte Invasion Protects Against Lethal Malaria," Proceedings of the National Academy of Sciences, Jul. 15, 2014, 111(28)10311-10316.
Stowers et al. "Structural conformers produced during malaria vaccine production in yeast." Yeast, Jan. 30, 2001, 18(2):137-150.
Sudhof et al. "The LDL Receptor Gene: A Mosaic of Exons Shared with Different Proteins," Science, 1985, 228(4701)815-822.
Supplementary Information (for Simon et al. Cell Host & Microbe 13, 29-41, Jan. 16, 2013, p. 1-27).
Surolia, Namita. "Receptor-mediated targeting of toxins to intraerythrocytic parasite Plasmodium falciparum." Advanced Drug Delivery Reviews, Mar. 1, 2000, 41(2):163-170.
Suzuki et al. "Structure and Expression of Human Thrombomodulin, a Thrombin Receptor on Endothelium Acting as a Cofactor for Protein C Activation," The EMBO Journal, 1987, 6(7)1891-1897.
Tachibana et al. "N-terminal Prodomain of Pfs230 Synthesized Using a Cell-Free System is Sufficient to Induce Complement-Dependent Malaria Transmission-Blocking Activity," Clinical and Vaccine Immunology, Aug. 2011, 18(8)1343-50.
Tamminga et al. "Human Adenovirus 5-vectored Plasmodium falciparum NMRC-M3V-Ad-PfCA Vaccine Encoding CSP and AMA1 is Safe, Well-Tolerated and Immunogenic But Does Not Protect Against Controlled Human Malaria Infection," Human Vaccines & Immunotherapeutics, Oct. 4, 2013, 9(10)2165-2177.
Tan et al. "Crystal Structure of the TSP-1 Type 1 Repeats: A Novel Layered Fold and Its Biological Implication," The Journal of Cell Biology, 2002, 159(2)373-382.
Taylor, W.R. "The Classification of Amino Acid Conservation," Journal of Theoretical Biology, 1986, 119:205-218.
Taylor et al. "A Transgenic Mouse that Expresses a Diversity of Human Sequence Heavy and Light Chain Immunoglobulins." Nucleic Acids Research, 1992, 20(23): 6287-6295.
Tiller et al. "Efficient Generation of Monoclonal Antibodies from Single Human B Cells by Single Cell RT-PCT and Expression Vector Cloning." Journal of Immunological Methods, Jan. 1, 2008, 329(1-2):112-124.
Tossavainen et al. "The Layered Fold of the TSR Domain of P. Falciparum TRAP Contains a Heparin Binding Site," Protein Science, 2006, 15(7)1760-1768.
Trucco et al. "The Merozoite Surface Protein 6 Gene Codes for a 36 kDa Protein Associated with the Plasmodium Falciparum Merozoite Surface Protein-1 Complex," Molecular & Biochemical Parasitology, 2001,112:91-101.
Tsuboi et al. "Wheat Germ Cell-Free System-Based Production of Malaria Proteins for Discovery of Novel Vaccine Candidates," Infection and Immunity, Apr. 2008, 76(4):1702-1708.
Tucker, R.P. "The Thrombospondim Type 1 Repeat Family," International Journal of Biochemistry & Cell Biology, 2004,36:969-974.
Uchime et al. "Analysis of the Conformation and Function of the Plasmodium falciparum Merozoite Proteins MTRAP and PTRAMP," Eukaryotic Cell, 2012, 11(5)615-625.
Vajdos et al. "Comprehensive Functional Maps of the Antigen-Binding Site of an Anti-ErbB2 Antibody Obtained with Shotgun Scanning Mutagenesis," Journal of Molecular Biology, 2002, 320: 415-428.
Vaquero et al. "Transient Expression of a Tumor-Specific Single-Chain Fragment and a Chimeric Antibody in Tobacco Leaves," Proceedings of the National Academy of Sciences of the United States of America, 1999, 96(20) 11128-11133.
Wasmuth et al. "The Origins of Apicomplexan Sequence Innovation," Genome Research, 2009, 19(7)1202-1213.
Wong et al. "Heating Greatly Speeds Coomassie Blue Staining and Destaining," Biotechniques, 2000, 28(3)426-432.
Wu et al. "Humanization of a Murine Monoclonal Antibody by Simultaneous Optimization of Framework and CDR Residues," Journal of Molecular Biology, 1999, 294:151-162.

(56) References Cited

OTHER PUBLICATIONS

Yoshida et al. "Bacteria expressing single-chain immunotoxin inhibit malaria parasite development in mosquitoes." Molecular and Biochemical Parasitology, Mar. 1, 2001, 113(1):89-96, Elsevier Science Publishers, Amsterdam, NL.
EP14719741.2 Communication Pursuant to Article 94(3) EPC dated Jun. 7, 2017.
JP2018-503823 Office Action dated Aug. 20, 2019.
PCT/EP2013/066086 International Search Report dated Oct. 21, 2013.
PCT/EP2014/058409 International Search Report dated Jul. 17, 2014.
PCT/EP2015/056693 International Search Report dated Jul. 27, 2015.
PCT/EP2015/069247 International Search Report dated Jan. 20, 2016.
PCT/EP2015/070044 International Search Report dated Apr. 11, 2015.
PCT/EP2016/077098 International Search Report dated Mar. 1, 2017.
Altschul et al. "Basic Local Alignment Search Tool," Journal of Molecular Biology, 1990, 215:403-410.
Anderson, Laura Fay. "Malaria Proteins Implicated in Host-Parasite," PhD Thesis, University of Edinburgh, 2006, p. 1-267.
Appella et al. "The Receptor-Binding Sequence of Urokinase. A Biological Function for the Growth-Factor Module of Proteases," The Journal of Biological Chemistry, 1987, 262(10)4437-4440.
Arama et al. "The Path of Malaria Vaccine Development: Challenges and Perspectives," Journal of Internal Medicine, May 18, 2014, 275(5)456-466.
Ausubel et al. "Current Protocols in Molecular Biology," Molecular Reproduction and Development, 1989, 1:146.
Barry et al. "Strategies for Designing and Monitoring Malaria Vaccines Targeting Diverse Antigens," Frontiers in Immunology, Jul. 28, 2014, 5(359)1-16.
Baum et al. "A Conserved Molecular Motor Drives Cell Invasion and Gliding Motility Across Malaria Life Cycle Stages and Other Apicomplexan Parasites," The Journal of Biological Chemistry, Feb. 24, 2006, 281(8): 5197-5208.
Beier et al. "Effects of Para-aminobenzoic Acid, Insulin, and Gentamicin on Plasmodium Falciparum Development in Anopheline Mosquitoes (Diptera: Culicidae)," Journal of Medical Entomology, 1994, 31(4)561-565.
Bergmann-Leitner et al. "Immunization with Pre-erythrocytic Antigen CeITOS from Plasmodium Falciparum Elicits Cross-Species Protection Against Heterologous Challenge with Plasmodium Berghei," PLoS One, 2010, 5(8)e12294.
Bird et al. "Single-Chain Antigen-Binding Proteins," Science, Oct. 21, 1988, 242(4877):423-426.
Bisaro et al. "Communications in Molecular Biology Viral Vectors," Cold Spring Harbor Laboratory, 1988, pp. 172-189, Cold Spring Harbor, NY.
Bishop et al. "Experiments Upon the Feeding of Aedes Aegypti Through Animal Membranes with a View to Applying the Method to the Chemotherapy of Malaria," Parasitology, 1946, 37:85-100.
Black et al. "Merozoite Surface Protein 8 of Plasmodium Falciparum Contains Two Epidermal Growth Factor-Like Domains," Molecular & Biochemical Parasitology, 2001, 114:217-226.
Black et al. "Apical location of a novel EGF-like domain-containing protein of Plasmodium falciparum." Molecular and Biochemical Parasitology, Mar. 2003, 127(1):59-68.
Blackman et al. "Proteolytic Processing of the Plasmodium Falciparum Merozoite Surface Protein-1 Produces a Membrane-Bound Fragment Containing Two Epidermal Growth Factor-Like Domains," Molecular & Biochemical Parasitology, 1991, 49(1)29-34.
Boerner et al. "Production of Antigen-Specific Human Monoclonal Antibodies from In Vitro-Primed Human Splenocytes" Journal of Immunology, Jul. 1, 1991, 147(1):86-95.

Boes et al. "Affinity Purification of a Framework 1 Engineered Mouse/Human Chimeric IgA2 Antibody From Tobacco," Biotechnology and Bioengineering, 2011, 108(12)2804-14.
Boes et al. "Analysis of a Mutli-Component Mutli-Stage Malaria Vaccine Candidate—Tackling the Cocktail Challenge," PLoS One, Jul. 6, 2015, 10(7):e0131456, https://doi.org/10.1371/journal.pone.0131456.
Bosch et al. "Crystal Stucture of GAP50, the Anchor of the Invasion Machinery in the Inner Membrane Complex of Plasmodium Falciparum." Journal of Structural Biology, 2012, 178:61-73.
Bowie et al. "Deciphering the Message in Protein Sequences: Tolerance to Amino Acid Substitutions," Science, Mar. 16, 1990, 247(4948)1306-1310.
Breedveld, FC, "Therapeutic Monoclonal Antibodies," Feb. 26, 2000, The Lancet, 355:735-740.
Brochet et al. "IMGT/V-QUEST: The Highly Customized and Integrated System for IG and TR Standardized V-J and V-D-J Sequence Analysis," Nucleic Acids Research, 2008, 36:W503-508.
Burgess et al. "Possible Dissociation of the Heparin-Binding and Mitogenic Activities of Heparin-binding (Acidic Fibroblast) Growth Factor-1 from Its Receptor-binding Activities by Site-Directed Mutagenesis of a Single Lysine Residue," Journal of Cell Biology, Nov. 1990, 1111:2129-2138.
Casset et al, "A Peptide Mimetic of an Anti-CD4 Monoclonal Antibody by Rational Design," Biochemical and Biophysical Research Communications, 2003, 307:198-205.
Chen et al. "Selection and Analysis of an Optimized Anti-VEGF Antibody: Crystal Structure of an Affinity-matured Fab in Complex with Antigen," Journal of Molecular Biology, 1999, 293:865-881.
Chen et al. "Opportunities and Challenges of Developing Thermostable Vaccines." Expert Rev. Vaccines, 2009, 8(5)547-557.
Chen et al. "An EGF-Like Protein Forms a Complex with PfRh5 and is Required for Invasion of Human Erythrocytes by Plasmodium Falciparum," PLoS Pathogen, Sep. 2011, 7(9)e1002199.
Chothia et al. "Conformations of Immunoglobulin Hypervariable Regions," Nature, 1989, 342:877-883.
Coley et al. "Structure of the Malaria Antigen AMA1 in Complex with a Growth-Inhibitory Antibody." Plos Pathogens, Sep. 2007, 3(9):e138.
Crompton et al. "Advances and Challenges in Malaria Vaccine Development," The Journal of Clinical Investigation, Dec. 2010, 120(12):4168-4178.
De Silva et al. "The Antibody Response to Plasmodium Falciparum Merozoite Surface Protein 4: Comparative Assessment of Specificity and Growth Inhibitory Antibody Activity to Infection-Acquired and Immunization-Induced Epitopes," Malaria Journal, 2011, 10(266):1-12.
Epping et al. "An Epitope Recognised by Inhibitory Monoclonal Antibodies that React with a 51 Kilodalton Merozoite Surface Antigen in Plasmodium Falciparum," Molecular & Biochemical Parasitology, 1988, 28(1)1-10.
Faber et al. "Diversity Covering AMA1-MSP119 Fusion Proteins as Malaria Vaccines," Infection and Immunity, May 2013, 81(5)1479-1490.
Furie et al. "The Molecular Basis of Blood Coagulation," Cell, 1988, 53(4)505-518.
Garcia-Basteiro et al. "Approaching the Target: the Path Towards an Effective Malaria Vaccine," Mediterranean Journal of Hematology and Infectious Diseases, 2012, 4(1)e2012015.
Geysen et al. "Use of Peptide Synthesis to Probe Viral Antigens for Epitopes to a Resolution of a Single Amino Acid," Proceedings of the National Academy of Sciences of the United States of America, Jul. 1984, 81:3998-4002.
Giraldo et al. "Vaccination with recombinant Plasmodium vivax MSP-10 formulated in different adjuvants induces strong immunogenicity but no protection." Vaccine, Dec. 10, 2009, 28(1):7-13, Elsevier Ltd, Germany.
Greenspan et al. "Defining Epitopes: It's Not as Easy as it Seems," Nature Biotechnology, 1999, 17:936-937.
Gosselin et al. "Enhanced Antigen Presentation Using Human Fc Gamma Receptor (Monocyte/Macrophage)—Specific Immunogens," Journal of Immunology, 1992, 149(11)3477-3481.

(56) References Cited

OTHER PUBLICATIONS

Grierson et al. "Plant Viruses," Plant Molecular Biology, 1988, pp. 126-146, Blackie, London.

Hagemeyer et al. "Single-chain antibodies as diagnostic tools and therapeutic agents" Thrombosis and Haemostasis, Jun. 2009, 101(6):1012-1019.

Harmsen et al. "Properties, production, and Applications of Camelid Single-Domain Antibody Fragments." Applied Microbiology and Biotechnology, 2007, 77: 13-22.

Hehmann-Titt et al. "Improving the therapeutic potential of human granzyme B for targeted cancer therapy." Antibodies, Jan. 16, 2013, 2(1):19-49.

Holliger et al. "'Diabodies': Small Bivalen and Bispecific Antibody Fragments." Proceedings of the National Academy of Science, USA, Jul. 1993, 90:6444-6448.

Hoogenboom et al. "By-Passing Immunisation Human Antibodies from Synthetic Repertoires of Germline Vh Gene Segments Rearranged in Vitro." Journal of Molecular Biology, 1992, 227:381-388.

Hu et al. "Minibody: A Novel Engineered Anti-Carcinoembryonic Antigen Antibody Fragment (Single-Chain Fv-Ch3) Which Exhibits Rapid, High-Level Targeting of Xeongrafts." Cancer Research, Jul. 1, 1996, 56:3055-3061.

Hugel et al. "Release of Malaria Circumsporozoite Protein into the Host Cell Cytoplasm and Interaction with Ribosomes," Molecular & Biochemical Parasitology, 1996, 81(2)151-170.

Huston et al. "Protein Engineering of Antibody Binding Sites: Recovery of Specific Activity in an Anit-Digoxin Single-Chain Fv Analogue Produced in *Escherichia coli*." Proceedings of the National Academy of Sciences, USA, Aug. 1988, 85:5879-5883.

Ifediba et al. "Complete In Vitro Maturation of Plasmodium Falciparum Gametocytes," Nature, 1981, 294(5839)364-366.

Imam et al. "Comparative Immunogenecities of Full-Length Plasmodium Falciparum Merozoite Surface Protein 3 and a 24-Kilodalton N-Terminal Fragment," Clinical Vaccine Immunology, Aug. 2011, 18(8): 1221-1228.

\* cited by examiner

Annotated amino acid sequence of the apical membrane antigen 1 (AMA-1)
(SEQ ID NO: 15)

FIGURE 4

Complete heavy chain (V heavy chain) variable regions (SEQ ID NO: 14) and light chain (V kappa) variable region (SEQ ID NO: 13) of huMAb-anti-AMA-1.1, represented according to Kabat definition (A) and IMGT definition (B)

A)

| | Framework 1 | CDR 1 | Framework 2 | CDR 2 | Framework 3 | CDR 3 | Framework 4 |
|---|---|---|---|---|---|---|---|
| V heavy chain | QVQLQQSGPGLVKPSETLSLTCSVSGVS | SIVFYWG | WIRQSPGKGLEWIG | SIYYSGSSTYYNPSLKS | RVTLSVDTSKNQFSLRLSSVTAADTAVYYCAR | GRLMEGGYSGPGTFYFDI | WGQGTLVTVSS |
| V kappa chain | DIQMTQSPSTLSASVGDRVTITCRAS | QSITTIW | LAWYQQKPGKAPKLLIY | KASILET | GVPSRFSGSGSGTEFTLTISSLQPDDFATYYC | QQYSTHLFT | FGGGTKVDIK |

B)

| | Framework 1 | CDR 1 | Framework 2 | CDR 2 | Framework 3 | CDR 3 | Framework 4 |
|---|---|---|---|---|---|---|---|
| V heavy chain | QVQLQQSGPGLVKPSETLSLTCSVS | GVSISSTVFY | WGWIRQSPGKGLEWIGS | IYYSGSST | YYNPSLKSRVTISVDTSKNQFSLRLSSVTAADTAVYYC | ARGRLMEGGYSGPGTFYFDI | WGQGTLVTVSS |
| V kappa chain | DIQMTQSPSTLSASVGDRVTITCRAS | QSITTW | LAWYQQKPGKAPKLLIY | KAS | ILETGVPSRFSGSGSGTEFTLTISSLQPDDFATYYC | QQYSTHLFT | FGGGTKVDIK |

FIGURE 9 huMAb-anti-MSP10.1 rel. IC$_{50}$ [%]

humAbAMA1 rel. IC$_{50}$ [%]

```
                         SEQUENCE LISTING

<160> NUMBER OF SEQ ID NOS: 18

<210> SEQ ID NO 1
<211> LENGTH: 11
<212> TYPE: PRT
<213> ORGANISM: Homo sapiens

<400> SEQUENCE: 1

Arg Ala Ser Gln Ser Ile Thr Thr Trp Leu Ala
1               5                   10

<210> SEQ ID NO 2
<211> LENGTH: 7
<212> TYPE: PRT
<213> ORGANISM: Homo sapiens

<400> SEQUENCE: 2

Lys Ala Ser Ile Leu Glu Thr
1               5

<210> SEQ ID NO 3
<211> LENGTH: 9
<212> TYPE: PRT
<213> ORGANISM: Homo sapiens

<400> SEQUENCE: 3

Gln Gln Tyr Ser Thr His Leu Phe Thr
1               5

<210> SEQ ID NO 4
<211> LENGTH: 7
<212> TYPE: PRT
<213> ORGANISM: Homo sapiens

<400> SEQUENCE: 4

Ser Thr Val Phe Tyr Trp Gly
1               5

<210> SEQ ID NO 5
<211> LENGTH: 16
<212> TYPE: PRT
<213> ORGANISM: Homo sapiens

<400> SEQUENCE: 5

Ser Ile Tyr Tyr Ser Gly Ser Thr Tyr Tyr Asn Glu Ala Leu Lys Ser
1               5                   10                  15
```

<210> SEQ ID NO 6
<211> LENGTH: 18
<212> TYPE: PRT
<213> ORGANISM: Homo sapiens

<400> SEQUENCE: 6

Gly Ala Ile Asn Phe Gly Gly Tyr Ser Gly Pro Gly Thr Phe Tyr Phe
1               5                   10                  15

Asp Ile

<210> SEQ ID NO 7
<211> LENGTH: 33
<212> TYPE: DNA
<213> ORGANISM: Homo sapiens

<400> SEQUENCE: 7
cgggccagtc agagtattac tacctggttg gcc                                33

<210> SEQ ID NO 8
<211> LENGTH: 21
<212> TYPE: DNA
<213> ORGANISM: Homo sapiens

<400> SEQUENCE: 8
aaggcgtcta ttttagagac t                                            21

<210> SEQ ID NO 9
<211> LENGTH: 27
<212> TYPE: DNA
<213> ORGANISM: Homo sapiens

<400> SEQUENCE: 9
caacagtata gtactcacct attcact                                      27

<210> SEQ ID NO 10
<211> LENGTH: 21
<212> TYPE: DNA
<213> ORGANISM: Homo sapiens

<400> SEQUENCE: 10
agtactgtgt tctactgggg c                                            21

<210> SEQ ID NO 11
<211> LENGTH: 48
<212> TYPE: DNA
<213> ORGANISM: Homo sapiens

<400> SEQUENCE: 11
agtatctatt atagtggtag cacgtactac aatgaggccc tcaagagc                48

<210> SEQ ID NO 12
<211> LENGTH: 54
<212> TYPE: DNA
<213> ORGANISM: Homo sapiens

<400> SEQUENCE: 12
ggggcgatta attttggggg atattcgggc cccgggacct tctattttga catt          54

<210> SEQ ID NO 13
<211> LENGTH: 107
<212> TYPE: PRT
<213> ORGANISM: Homo sapiens

<400> SEQUENCE: 13

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Thr Thr Trp
            20                  25                  30

Leu Ala Trp Tyr Gln Gln Lys Pro Gly Thr Ala Pro Lys Leu Leu Ile
        35                  40                  45

Tyr Lys Ala Ser Ile Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Thr His Leu Phe
                85                  90                  95

Thr Phe Gly Pro Gly Thr Lys Val Asp Ile Lys
            100                 105
```

<210> SEQ ID NO 14
<211> LENGTH: 128
<212> TYPE: PRT
<213> ORGANISM: Homo sapiens

<400> SEQUENCE: 14

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Val Ser Ser Thr
            20                  25                  30

Val Phe Tyr Trp Gly Trp Ile Arg Gln Ser Pro Gly Lys Gly Leu Glu
        35                  40                  45

Trp Ile Gly Ser Ile Tyr Tyr Ser Gly Ser Thr Tyr Tyr Asn Glu Ala
50                  55                  60

Leu Lys Ser Arg Leu Thr Leu Ser Val Glu Thr Ser Glu Arg Gln Phe
65                  70                  75                  80

Ser Leu Arg Leu Ser Ser Val Thr Ala Ala Asp Thr Ala Val Tyr Tyr
                85                  90                  95

Cys Ala Arg Gly Ala Ile Asn Phe Gly Gly Tyr Ser Gly Pro Gly Thr
            100                 105                 110

Phe Tyr Phe Asp Ile Trp Gly Gln Gly Thr Leu Ile Thr Val Ser Ser
        115                 120                 125
```

<210> SEQ ID NO 15
<211> LENGTH: 622
<212> TYPE: PRT
<213> ORGANISM: Plasmodium falciparum

<400> SEQUENCE: 15

```
Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
50                  55                  60

Asp Ser Gly Glu Asp Glu Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95
```

```
Ile Glu Ile Val Glu Arg Ser Asn Tyr Met Gly Asn Pro Trp Thr Glu
                100                 105                 110

Tyr Met Ala Lys Tyr Asp Ile Glu Glu Val His Gly Ser Gly Ile Arg
                115                 120                 125

Val Asp Leu Gly Glu Asp Ala Glu Val Ala Gly Thr Gln Tyr Arg Leu
            130                 135                 140

Pro Ser Gly Lys Cys Pro Val Phe Gly Lys Gly Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
        210                 215                 220

Ile Pro Asp Asn Asp Lys Asn Ser Asn Tyr Lys Tyr Pro Ala Val Tyr
225                 230                 235                 240

Asp Asp Lys Asp Lys Cys His Ile Leu Tyr Ile Ala Ala Gln Glu
            245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
        290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
            325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
        355                 360                 365

Asn Lys Asn Ala Ser Met Ile Lys Ser Ala Phe Leu Pro Thr Gly Ala
370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
            405                 410                 415

Thr Cys Leu Ile Asn Asn Ser Ser Tyr Ile Ala Thr Thr Ala Leu Ser
        420                 425                 430

His Pro Ile Glu Val Glu Asn Asn Phe Pro Cys Ser Leu Tyr Lys Asp
        435                 440                 445

Glu Ile Met Lys Glu Ile Glu Arg Glu Ser Lys Arg Ile Lys Leu Asn
    450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
            485                 490                 495

Val Ser Asn Ser Thr Cys Arg Phe Phe Val Cys Lys Cys Val Glu Arg
            500                 505                 510
```

```
Arg Ala Glu Val Thr Ser Asn Asn Glu Val Val Lys Glu Glu Tyr
        515                 520                 525

Lys Asp Glu Tyr Ala Asp Ile Pro Glu His Lys Pro Thr Tyr Asp Lys
    530                 535                 540

Met Lys Ile Ile Ile Ala Ser Ser Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Lys Arg
        595                 600                 605

Ala Ser His Thr Thr Pro Val Leu Met Glu Lys Pro Tyr Tyr
    610                 615                 620

<210> SEQ ID NO 16
<211> LENGTH: 206
<212> TYPE: PRT
<213> ORGANISM: Plasmodium falciparum

<400> SEQUENCE: 16

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Glu Asn
    50                  55                  60

Ser Asn Thr Thr Phe Leu Thr Pro Val Ala Thr Gly Asn Gln Tyr Leu
65                  70                  75                  80

Lys Asp Gly Gly Phe Ala Phe Pro Pro Thr Glu Pro Leu Met Ser Pro
                85                  90                  95

Met Thr Leu Asp Glu Met Arg His Phe Tyr Lys Asp Asn Lys Tyr Val
            100                 105                 110

Lys Asn Leu Asp Glu Leu Thr Leu Cys Ser Arg His Ala Gly Asn Met
        115                 120                 125

Ile Pro Asp Asn Asp Lys Asn Ser Asn Tyr Lys Tyr Pro Ala Val Tyr
    130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Glu Ser Lys Arg Asn Ser Met
                165                 170                 175

Phe Cys Phe Arg Pro Ala Lys Asp Ile Ser Phe Gln Asn Tyr Thr Tyr
            180                 185                 190

Leu Ser Lys Asn Val Val Asp Asn Trp Glu Lys Val Cys Pro
        195                 200                 205

<210> SEQ ID NO 17
<211> LENGTH: 23
<212> TYPE: DNA
<213> ORGANISM: Artificial Sequence
<220> FEATURE:
<223> OTHER INFORMATION: Sythesized Primer

<400> SEQUENCE: 17
atccttcgca agacccttcc tct                                            23
```

-continued

```
<210> SEQ ID NO 18
<211> LENGTH: 23
<212> TYPE: DNA
<213> ORGANISM: Artificial Sequence
<220> FEATURE:
<223> OTHER INFORMATION: Syntesized Primer

<400> SEQUENCE: 18
agagagagat agatttgtag aga                                    23
```

ANTI-PLASMODIUM PARASITE ANTIBODIES

CROSS REFERENCE TO RELATED APPLICATIONS

This is a US national phase application under 35 USC § 371 of international patent application no. PCT/EP2016/057873, filed Apr. 11, 2016, which itself claims priority to European application 15163297.3, filed Apr. 12, 2015. Each of the applications referred to in this paragraph are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with file "PCTEP2016057873_2017_10_SEQID" created on 12 Oct. 2017, filed on 12 Oct. 2017 and having a size of 12 Kilobytes. The sequence listing contained in this ASCII formatted document forms part of the specification and is herein incorporated by reference in its entirety.

FIELD OF THE DISCLOSURE

The technology provided herein relates to novel human antibodies against *Plasmodium* parasites, in particular against the malaria parasite *Plasmodium falciparum*. The present disclosure pertains to antibodies against apical membrane antigen 1 (AMA-1). These antibodies have high affinity e.g. to *Plasmodium falciparum* schizonts and merozoites, inhibit the reinvasion of merozoites into erythrocytes and thereby neutralize parasitic multiplication.

An antibody of the present disclosure can be a full-length antibody or an antigen-binding portion thereof. Furthermore, an antibody of the present disclosure or an antigen-binding portion thereof may be used as a cell-specific binding domain in a complex comprising the binding domain and an effector domain. Nucleic acid molecules encoding said antibodies and complexes, vectors, host cells containing the nucleic acids and methods for preparation and producing such antibodies; compositions and methods for using such antibodies for the treatment of malaria are also encompassed by the present disclosure.

BACKGROUND

About 3.3 billion people—half of the world's population—are at risk of malaria. In the year 2012, this led to about 207 million malaria cases and approx. 627,000 deaths (World Health Organization 2013). Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum* (causing Malaria tropica), *P. vivax* (causing Malaria tertiana), *P. ovale* (causing Malaria tertiana), *P. knowlesi* (causing Malaria quotidiana) and *P. malariae* (causing Malaria quartana). Each of these species is transmitted to the human via female Anopheles mosquitoes that transmit *Plasmodium* parasites in the stage of sporozoites. Once the sporozoites enter the bloodstream of the human, they localize in liver cells, i.e. hepatocytes. One to two weeks later, the infected hepatocytes rupture and release merosomes. These merosomes circulate in the blood stream for short time before releasing merozoites. These then begin the erythrocytic phase of malaria by attaching to and invading red blood cells, or erythrocytes. The erythrocytic stage of the life cycle begins, which is the direct cause of malarial pathogenesis and pathology. The fever, anemia, circulatory changes, and immunopathologic phenomena characteristic of malaria are largely the result of red cell rupture and the host's immune response to parasite antigen and hemozoin. For these reasons, the erythrocytic stage of the *Plasmodium* life cycle is of vital importance to passive or active vaccine development and treatment of malaria.

Malaria caused by *Plasmodium falciparum* (also called malignant malaria, falciparum malaria or malaria tropica) is the most dangerous form of malaria, with the highest rates of complications and mortality. Almost all malarial deaths are caused by *P. falciparum*.

Resistance of *Plasmodium falciparum* to the existing anti-malarial drug chloroquine emerged in the sixties of the last century in asia and has spread worldwide since then. In addition, the malaria parasite has developed resistance to most other anti-malarial drugs over the past decade. This poses a major threat to public health. There is every reason to believe that the prevalence and degree of anti-malarial drug resistance will continue to increase. Furthermore, many anti-malaria drugs have been notorious for their toxic side effects, e. g. mefloquin. Today, the recommended treatments against *Plasmodium falciparum* malaria are artemisinin-based combination therapies. But also against this therapy, resistances start to occur in different parts of the world, e.g. Kenya and Cambodia (Borrmann et al. 2011; Noedl, Socheat, and Satimai 2009).

In principle, antibodies against *Plasmodium falciparum* with appropriate specificity and activity are desirable as an anti-malaria drug. Human antibodies would be advantageous over non-human antibodies and humanized, chimeric antibodies for use in human therapy for several reasons: A human antibody is less likely to induce an immunological response in humans than antibodies that contain non-human portions. This immune response against non-human portions rules out the possibility of repeated therapies with such antibodies. In conclusion, human antibodies can be used multiple times as a treatment regimen. Furthermore, a human antibody is less likely to be recognized as a "foreign" antibody in humans. This will result in neutralization or slower elimination of the human antibody from the body than a non-human or partially human antibody. Accordingly, a human antibody can be administered at lower doses or the treatment regimen can be adapted to lower frequency than non-human or partially human antibodies.

Therefore the availability of novel human antibodies to inhibit the growth and/or invasion of *Plasmodium* parasites, in particular for the treatment of malaria infected individuals, would be highly advantageous.

SUMMARY OF THE INVENTION

The present disclosure relates to novel isolated human antibodies or antigen-binding portions thereof for preventing, treating and/or the diagnosis/detecting of *Plasmodium* parasites, in particular for the treatment preventing, treating and/or the diagnosis of malaria.

In a first aspect, embodiments of the disclosure relate to isolated human antibodies, or antigen-binding portions thereof, that bind to apical membrane antigen 1 (AMA-1) of *Plasmodium* parasites, in particular to AMA-1 of *Plasmodium falciparum*.

In particular, isolated human antibodies, or antigen-binding portions thereof, binds to apical membrane antigen 1 (AMA-1) of a *Plasmodium* parasite, in particular to AMA-1 of *Plasmodium falciparum*, or to AMA-1 of a plurality of different *Plasmodium* parasites, wherein said antibody or antigen-binding portion thereof inhibits the invasion of the *Plasmodium* parasite(s) into the erythrocyte and/or the growth of the *Plasmodium* parasite within the erythrocyte, in particular wherein the isolated antibody or antigen-binding portion thereof is a monoclonal antibody, an antibody from human B-cell cultures, a recombinant antibody, a synthetic antibody or an antigen-binding portion thereof.

In particular, embodiments of the disclosure relate to an isolated human antibody, or an antigen-binding portion thereof, that binds to apical membrane antigen 1 (AMA-1) of *Plasmodium* parasites, in particular to AMA-1 of *Plasmodium falciparum*, wherein said antibody or antigen-binding portion thereof inhibits the invasion of a *Plasmodium* parasite into the erythrocyte and/or the growth of the *Plasmodium* parasite within the erythrocyte, wherein the isolated antibody or antigen-binding portion thereof is a monoclonal antibody, an antibody from human B-cell cultures, a recombinant antibody, a synthetic antibody or an antigen-binding portion thereof, and wherein said isolated human antibody, or an antigen-binding portion thereof has a light chain variable region (LCVR) comprising CDR1 of SEQ ID NO:1, CDR2 of SEQ ID NO:2 and CDR3 of SEQ ID NO:3, and a heavy chain variable region (HCVR) comprising CDR1 of SEQ ID NO:4, CDR2 of SEQ ID NO:5 and CDR3 of SEQ ID NO:6.

In a second aspect, embodiments of the disclosure relate to isolated human antibodies, or antigen-binding portions thereof, that bind specific to AMA-1 of *Plasmodium falciparum* comprising SEQ ID NO. 15, and/or that bind specific to domain I of AMA-1 of *Plasmodium falciparum* comprising SEQ ID NO.16.

In a further aspect, embodiments of this disclosure relate to isolated human antibodies, or antigen-binding portions thereof, having a light chain variable region (LCVR) and a heavy chain variable region (HCVR) and comprising at least two polypeptides having a sequence selected from SEQ ID NOs: 1, 2, 3, 4, 5 and 6, wherein the antibody inhibits the growth of *Plasmodium* parasites, in particular of *Plasmodium falciparum*.

Furthermore, embodiments of the present disclosure relate to isolated human antibodies, or antigen-binding portions thereof, wherein the light chain variable region (LCVR) comprises a polypeptide with the sequence shown in SEQ ID NO: 13 (shown in FIG. 4).

Furthermore, embodiments of the present disclosure relate to isolated human antibodies, or antigen-binding portions thereof, wherein the heavy chain variable region (HCVR) comprises a polypeptide with the sequence shown in SEQ ID NO: 14 (shown in FIG. 4).

Furthermore, embodiments of the present disclosure relate to isolated human antibodies, or antigen-binding portions thereof, wherein the light chain variable region (LCVR) comprises a polypeptide with the sequence shown in SEQ ID NO. 13 and the heavy chain variable region (HCVR) comprises a polypeptide with the sequence shown in SEQ ID NO: 14.

In still another aspect, embodiments of this disclosure provide nucleic acids encoding said isolated antibodies or antibody fragments/portions thereof, as well as vectors and host cells comprising such nucleic acids.

In other aspects, this disclosure relates to compositions comprising an isolated antibody or antibody an antibody fragment/portion thereof as described herein, wherein the compositions may be useful for, or used in therapeutically and/or diagnostic applications. In one advantageous embodiment, the composition is used as a therapeutical composition for the treatment of malaria, in particular of malaria tropica.

Therefore, embodiments of this disclosure relate to a pharmaceutical or diagnostic composition comprising an antibody or an antigen-binding portion thereof according to the present disclosure. In particular, said composition may comprise at least a further antibody or an antigen-binding portion thereof. In some embodiments, the isolated antibody or an antigen-binding portion thereof according to the present disclosure may inhibits the invasion of a *Plasmodium* parasite into the erythrocyte and/or the growth of a *Plasmodium* parasite synergistically in combination with another antibody or antigen-binding portion thereof.

In a further aspect, embodiments of this disclosure relate to methods for producing the antibodies or antibody fragments/portions thereof in a host cell by transforming the host cell with a DNA construct, advantageously including a promoter having transcriptional activity in the host cell, cultivating the transformed host cell in a suitable culture medium to allow expression of said antibodies and producing the antibodies or antibody fragments thereof. The method may also include recovering or isolating the produced antibodies or antibody fragments/portions thereof, and optionally processing the said antibodies or antibody fragments/portions thereof.

In a further aspect, the disclosure relates to purified complexes comprising an antibody or an antigen-binding portion thereof according to the present disclosure as a specific binding domain and an effector domain; medicaments comprising such a complex in combination with a pharmacologically acceptable carrier or diluent and the use of such a complex for treating malaria, in particular malaria tropica.

Before the disclosure is described in detail, it is to be understood that this disclosure is not limited to the particular disclosed embodiments. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 4 shows the complete heavy (SEQ ID NO: 14) and light chain (SEQ ID NO: 13) variable regions of huMAb-anti-AMA-1.1 with the framework regions and the complementarity determining regions highlighted. CDR regions and framework regions according to the Kabat definition (FIG. 4A) and according to the analysis of IMGT/V-Quest (FIG. 4B) are shown (Heavy chain sequence: SEQ ID NO. 14; Light chain sequence SEQ ID NO. 13).

FIG. 9 shows the isobologram representing the synergistic reactivity of the antibody huMAb-anti-AMA-1.1 with the antibody huMAb-anti-MSP10.1 using a growth inhibition assay (GIA).

DETAILED DESCRIPTION OF THE INVENTION

The present application discloses therapeutically and/or diagnostic useful isolated human antibodies, or antigen-binding portions thereof, specific for antigen-domains of the apical membrane antigen (AMA-1) of *Plasmodium* parasites, in particular of *Plasmodium falciparum* and characterized by high affinity binding to the parasite, and the functional capacity to inhibit the invasion of the *Plasmodium* parasites into the erythrocyte and/or the growth of the *Plasmodium* parasites within the erythrocyte. These characteristics make them specifically useful as a powerful therapeutic and/or diagnostic agent.

Figure 7:
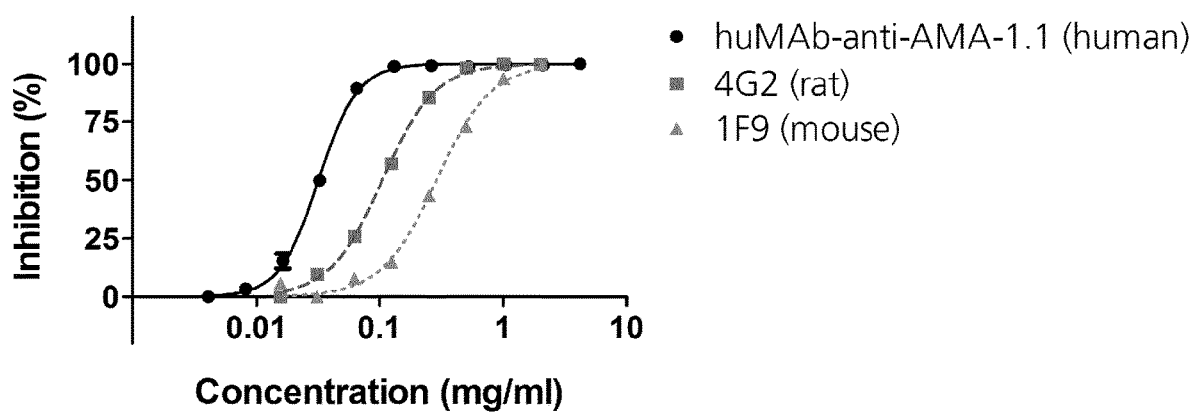
FIG. 7 shows the results of the growth inhibition assay (GIA) against the parasite strains 3D7 using the herewith disclosed antibody huMAb-anti-AMA-1.1 in comparison to described antibodies of rat (4G2) and murine (1F9) origin.

Surprisingly, the inventors found that the activity of the new fully human antibody according to the present disclosure e.g. the huMAb-anti-AMA-1.1 has a growth inhibitory activity which is higher than other anti-AMA-1 antibodies known so far. This human antibody inhibits the *Plasmodium falciparum* parasite at a concentration with an $IC_{50}$ of 32 µg/ml. The $IC_{50}$ of 4G2, a ratMAb-anti-AMA-1 antibody, has an $IC_{50}$ against the *P. falciparum* strain 3D7 of above 106 µg/ml, 1F9, a mouseMAb-anti-AMA-1 antibody, has an $IC_{50}$ against the *P. falciparum* strain 3D7 of 290 µg/ml (FIG. 7 and Table 7).

Figure 8:
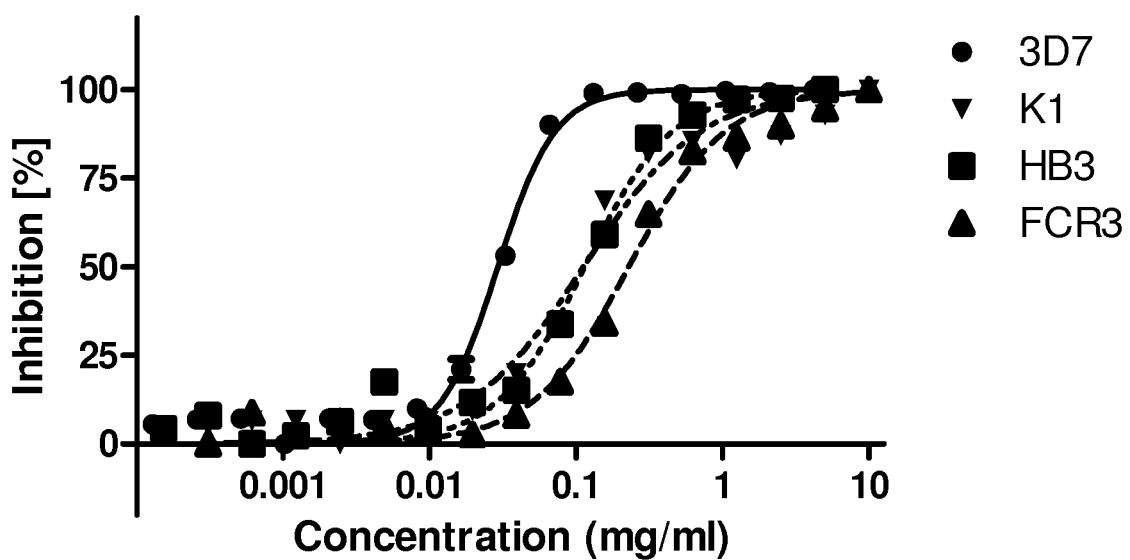
FIG. 8 shows the results of the growth inhibition assay (GIA) against the parasite strains 3D7, HB3, K1 and FCR3.

The antibody 1F9 binds to the same domain as the antibody huMAb-anti-AMA-1.1 disclosed herein. The antibody 1F9 is solely inhibitory towards the parasite strain 3D7, it shows no inhibitory activity against the parasite strains HB3, FCR3 or K1. Here, we are disclosing an antibody which has high reactivity towards multiple *P. falciparum* parasite strains, including 3D7, HB3, FCR3 and K1 (FIG. 8 and Table 8).

Therefore, in some advantageous embodiments, the isolated human antibodies, or an antigen-binding portions thereof according to the present disclosure bind to AMA-1 of a plurality of different *Plasmodium* parasites, in particular to AMA-1 of a plurality of different *Plasmodium falciparum* parasites including the *P. falciparum* parasite strains 3D7, HB3, FCR3 and K1.

An antibody is specific for a particular antigen if it binds that particular antigen in preference to other antigens. In particular, the antibody may not show any significant binding to molecules other than that particular antigen, and specificity may be defined by the difference in affinity between the target antigen and other non-target antigens. An antibody may also be specific for a particular epitope which may be carried by a number of antigens, in which case the antibody will be able to bind to the various antigens carrying that epitope. For example, specific binding may exist when the dissociation constant for a dimeric complex of antibody and antigen is 1 µM, preferably 100 nM and most preferably 1 nM or lower.

An antibody is an immunoglobulin molecule comprised of four polypeptide chains, two heavy (H) chains (about 50-70 kDa when full length) and two light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively.

Each heavy chain is comprised of a heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions (Chothia and Lesk 1987; Chothia et al. n.d.; Kabat et al. 1992). The functional ability of the antibody to bind a particular antigen is largely determined by the CDRs.

Accordingly, in a first aspect the present disclosure provides an isolated antibody, preferably an isolated recombinant human antibody or an antigen-binding portion thereof comprising an amino acid sequence specific for the antigen AMA-1 of *Plasmodium* parasites, in particular of *Plasmodium falciparum*.

In an advantageous embodiment, the antibodies of the present disclosure are specific for an epitope comprised in a polypeptide comprising the amino acid sequence shown in SEQ ID NO. 15. In particular, the antibodies of the present disclosure are specific for the domain I of AMA-1 (SEQ ID NO: 16). In an advantageous embodiment, SEQ ID NO. 15 corresponds to sequence of the *Plasmodium falciparum* antigen AMA-1 of the parasite strain 3D7 (Genbank entry XM_001347979). In an advantageous embodiment, the antibody is specific for the variations of AMA-1. In advantageous embodiments, the isolated human antibodies, or antigen-binding portions thereof, according to the present disclosure binds to AMA-1 derived from various/different *Plasmodium* parasites including *Plasmodium* parasites having the Genbank No. U33274 (strain 3D7), EU586390 (strain FCR-3), U33277 (strain HB3), U33279 (strain K1) or DQ218424 (strain Dd2).

In a further aspect, embodiments of this disclosure relate to isolated antibodies, isolated recombinant human antibodies or antigen-binding portion thereof, having a light chain variable region (LCVR) and a heavy chain variable region (HCVR) and comprises at least two polypeptides having a sequence selected from the SEQ ID NOs: 1, 2, 3, 4, 5 and 6, listed in Table 1, wherein the antibodies inhibit the growth of plasmodium parasites, in particular of *Plasmodium falciparum*. The complete antibody variable regions are represented in FIG. 4. Here, the CDR regions 1, 2 and 3 from the heavy and light chain are underlined.

This present disclosure provides isolated human antibodies, or antigen-binding portions thereof, that bind to apical membrane antigen 1 (AMA-1). Preferably, the human antibodies of the invention are recombinant, growth inhibiting human AMA-1 antibodies.

Table 1 shows the amino acid sequences of complementarity-determining regions 1-3 (CDR 1-3) of the antibodies' heavy and light chains.

TABLE 1

LCVR and HCVR of AMA-1-binding antibody huMAb-anti-AMA-1.1

| SEQ ID # | CDR # | Amino Acid Sequence according to Kabat definition (Martin 2010) |
|---|---|---|
| SEQ ID NO: 1 | CDR1 (VL) | RASQSITTWLA |
| SEQ ID NO: 2 | CDR2 (VL) | KASILET |
| SEQ ID NO: 3 | CDR3 (VL) | QQYSTHLFT |
| SEQ ID NO: 4 | CDR1 (VH) | STVFYWG |
| SEQ ID NO: 5 | CDR2 (VH) | SIYYSGSTYYNEALKS |
| SEQ ID NO: 6 | CDR3 (VH) | GAINFGGYSGPGTFYFDI |

In another advantageous embodiment, the disclosure provides an isolated human antibody, preferably an isolated recombinant human antibody or antigen-binding portion thereof, comprising at least one polypeptide, preferably at least 2, 3, 4, 5 or 6 polypeptides, with a sequence selected from the group consisting of the sequences shown in CDR1 of huMAb-anti-AMA-1.1 VH (SEQ ID NO: 4), CDR2 of huMAb-anti-AMA-1.1 VH (SEQ ID NO: 5), CDR3 of huMAb-anti-AMA-1.1 VH (SEQ ID NO: 6), CDR1 of huMAb-anti-AMA-1.1 VL (SEQ ID NO: 1), CDR2 of huMAb-anti-AMA-1.1 VL (SEQ ID NO: 2) or CDR3 of huMAb-anti-AMA-1.1 VL (SEQ ID NO: 3), wherein said polypeptides preferably exist in said antibody at the same CDR position as shown in Table 1 herein.

In some embodiments the LCVR comprises a polypeptide with the sequence shown in: CDR1 of huMAb-anti-AMA-1.1 VL (SEQ ID NO: 1), CDR2 of huMAb-anti-AMA-1.1 VL (SEQ ID NO: 2) or CDR3 of huMAb-anti-AMA-1.1 VL (SEQ ID NO: 3). In another embodiment, the disclosure provides a human antibody, or antigen-binding portion thereof, comprising a LCVR comprising a polypeptide with the sequence shown in: CDR1 of huMAb-anti-AMA-1.1 VL (SEQ ID NO: 1), CDR2 of huMAb-anti-AMA-1.1 VL (SEQ ID NO: 2) or CDR3 of huMAb-anti-AMA-1.1 VL (SEQ ID NO: 3), and further comprising a HCVR comprising a polypeptide with the sequence shown in CDR1 of huMAb-anti-AMA-1.1 VH (SEQ ID NO: 4), CDR2 of huMAb-anti-AMA-1.1 VH (SEQ ID NO: 5), CDR3 of huMAb-anti-AMA-1.1 VH (SEQ ID NO: 6).

According to an advantageous embodiment of the present disclosure, the LCVR CDR1 domain comprises the amino acid sequence of SEQ ID NO: 1. In another embodiment, the LCVR CDR2 domain comprises the amino acid sequence of SEQ ID NO: 2. In another embodiment, the LCVR CDR3 domain comprises the amino acid sequence of SEQ ID NO: 3.

According to another advantageous embodiment of the present disclosure, there is provided a LCVR CDR1 domain comprising the amino acid sequence of SEQ ID NO: 1 and a CDR2 domain comprising the amino acid sequence of SEQ ID NO: 2. In some embodiments the LCVR CDR1 domain comprises the amino acid sequence of SEQ ID NO: 1 and the LCVR CDR3 domain comprises the amino acid sequence of SEQ ID NO: 3. In some embodiments the LCVR CDR2 domain comprises the amino acid sequence of SEQ ID NO: 2 and the LCVR CDR3 domain comprises the amino acid sequence of SEQ ID NO: 3.

According to an advantageous embodiment of the present disclosure, the HCVR CDR1 domain comprises the amino acid sequence of SEQ ID NO: 4. In another embodiment, the HCVR CDR2 domain comprises the amino acid sequence of SEQ ID NO: 5. In another embodiment, the HCVR CDR3 domain comprises the amino acid sequence of SEQ ID NO: 6. According to another advantageous embodiment of the present disclosure, there is provided a HCVR CDR1 domain comprising the amino acid sequence of SEQ ID NO: 4 and a CDR2 domain comprising the amino acid sequence of SEQ ID NO: 5. In some embodiments the HCVR CDR1 domain comprises the amino acid sequence of SEQ ID NO: 4 and the HCVR CDR3 domain comprises the amino acid sequence of SEQ ID NO: 6. In some embodiments the HCVR CDR2 domain comprises the amino acid sequence of SEQ ID NO: 5 and the HCVR CDR3 domain comprises the amino acid sequence of SEQ ID NO: 6.

In another embodiment the LCVR comprises a polypeptide with the sequence shown in SEQ ID NO: 1 and the HCVR comprises a polypeptide with the sequence shown in SEQ ID NO: 4, or the LCVR comprises a polypeptide with the sequence shown in SEQ ID NO: 1 and the HCVR comprises a polypeptide with the sequence shown in SEQ ID NO: 5, or the LCVR comprises a polypeptide with the sequence shown in SEQ ID NO: 1 and the HCVR comprises a polypeptide with the sequence shown in SEQ ID NO: 6, or the LCVR comprises a polypeptide with the sequence shown in SEQ ID NO: 2 and the HCVR comprises a polypeptide with the sequence shown in SEQ ID NO: 4, or the LCVR comprises a polypeptide with the sequence shown in SEQ ID NO: 2 and the HCVR comprises a polypeptide with the sequence shown in SEQ ID NO: 5, or the LCVR comprises a polypeptide with the sequence shown in SEQ ID NO: 2 and the HCVR comprises a polypeptide with the sequence shown in SEQ ID NO: 6, or the LCVR comprises a polypeptide with the sequence shown in SEQ ID NO: 3 and the HCVR comprises a polypeptide with the sequence shown in SEQ ID NO: 4, or the LCVR comprises a polypeptide with the sequence shown in SEQ ID NO: 3 and the HCVR comprises a polypeptide with the sequence shown in SEQ ID NO: 5, or the LCVR comprises a polypeptide with the sequence shown in SEQ ID NO: 3 and the HCVR comprises a polypeptide with the sequence shown in SEQ ID NO: 6.

In an advantageous embodiment, the antibody according to the present disclosure is referred herein as huMAb-anti-AMA-1.1. The huMAb-anti-AMA-1.1 has LCVR and HCVR comprising the polypeptides having the sequences with SEQ ID NOs 1, 2, 3, 4, 5 and 6 or variant, mutants, modified form, homologue or derivative thereof, in particular having a conservative mutation.

Further embodiments of the present disclosure relate to isolated human antibodies, or antigen-binding portion thereof, wherein the light chain variable region (LCVR) comprises a polypeptide with the sequence shown in SEQ ID NO: 13 comprising SEQ ID NOs 1, 2 and 3.

Furthermore, embodiments of the present disclosure relate to isolated human antibodies, or antigen-binding portion thereof, wherein the heavy chain variable region (HCVR) comprises a polypeptide with the sequence shown in SEQ ID NO: 14 comprising SEQ ID NOs 4, 5 and 6.

Furthermore, embodiments of the present disclosure relate to isolated human antibodies, or antigen-binding portion thereof, wherein the light chain variable region (LCVR) comprises a polypeptide with the sequence shown in SEQ ID NO: 13 and the heavy chain variable region (HCVR) comprises a polypeptide with the sequence shown in SEQ ID NO: 14 (see FIG. 4).

The variable heavy chain regions discussed above may be combined with any suitable constant region, including the constant region of gamma 1, gamma 2, gamma 3, gamma 4, mu, alpha 1, alpha 2, delta or epsilon isotypes as well as any artificial constant region.

In an advantageous embodiment, the antibodies of the present disclosure has IgG1 heavy chain constant region. Alternatively, the antibodies of the present disclosure has IgG3 heavy chain constant region.

In addition to the complete antibody, fragments of the antibody may also have the ability to bind the appropriate antigen (such as AMA-1), and are therefore also encompassed by the present disclosure.

For example, it has been shown that fragments of a whole antibody can perform the function of binding antigens. Examples of binding fragments are (i) the Fab fragment consisting of LCVR, HCVR, CL and CH1 domains; (ii) the Fd fragment consisting of the HCVR and CH1 domains; (iii) the Fv fragment consisting of the LCVR and HCVR domains of a single antibody; (iv) the dAb fragment, (Ward et al. 1989), which consists of a HCVR domain; (v) isolated CDR regions; (vi) F (ab') 2 fragments, a bivalent fragment comprising two linked Fab fragments (vii) single chain Fv molecules (scFv), wherein a HCVR domain and a LCVR domain are linked by a peptide linker which allows the two domains to associate to form an antigen binding site (Bird et al. 1988; Huston et al. 1988); (viii) bispecific single chain Fv dimers (PCT/US92/09965) and (ix)"diabodies", multivalent or multispecific fragments constructed by gene fusion (WO94/13804; Holliger, Prospero, and Winter 1993). Fv, scFv or diabody molecules may be stabilised by the incorporation of disulphide bridges linking the HCVR and LCVR domains (Reiter et al. 1996). Minibodies comprising a scFv joined to a CH3 domain may also be made (Hu et al. 1996). In addition, nanobodies can be produced based on the disclosed sequence information (Harmsen and De Haard 2007).

In an advantageous embodiment, the isolated antigen binding portion is a Fab fragment. Alternatively, the isolated antigen binding portion is a F(ab')₂ fragment or a single chain Fv fragment.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. According to the present disclosure, the term "antibody" includes, but is not limited to recombinant antibodies, polyclonal antibodies, synthetic antibodies, monoclonal antibodies, single chain antibodies, humanized antibodies, minibodies, diabodies, tribodies as well as antibody fragments, including antigen-binding portion of the antibodies according to the present disclosure, such as Fab', Fab, F(ab')₂ and single domain antibodies as mentioned above. In advantageous embodiments the term "antibody" refers to a recombinant antibody, in particular to a recombinant human antibody or an antigen-binding portion thereof. The term includes also isolated antibodies like a monoclonal antibody, e.g. produced in a hybridoma cell. In advantageous embodiments, the isolated human antibody according to the present disclosure is a monoclonal antibody.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As notified above, the term "antigen-binding portion" of an antibody (or "antibody portion") includes fragments of an antibody that retains the ability to specifically bind to an antigen (e.g., AMA-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. 1989), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)) (Bird et al. 1988; Huston et al. 1988). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (Holliger et al. 1993; Poljak 1994). Still further, an antibody or antigen-binding portion thereof may be part of larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov et al. 1995) and use of a cysteine residue, a marker peptide and a C-terminal polyhistidine tag to make bivalent and biotinylated scFv molecules (Kipriyanov et al. 1994). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

In an advantageous embodiment, the antibodies or antigen-binding portion thereof according to the present disclosure are human or humanized antibodies. In advantageous embodiments the antibodies are recombinant antibodies. In some examples the antibodies have an IgG1 heavy chain constant region. Alternatively, the antibodies according to the present disclosure are antigen-binding portions like Fab fragments, F(ab')$_2$ or single chain Fv fragments.

The term "human antibody" includes antibodies having variable and constant regions corresponding to human germline immunoglobulin sequences as described by Kabat et al. (Kabat et al. 1992). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The mutations preferably are introduced using the "selective mutagenesis approach" described herein. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below. However, the term "human antibody", as used herein, is not intended to include antibodies in which CDR sequences derived from the germline of another mammalian species, such as a mouse, have been grafted onto human framework sequences. Furthermore, the term "human antibody" as used herein, is (i) an intact antibody, (ii) a substantially intact antibody, (iii) a portion of an antibody comprising an antigen-binding site, or (iv) a portion of an antibody comprising a Fab fragment, Fab' fragment or F(ab')$_2$, having variable and constant regions encoded by nucleic acid sequence information that occurs in the human germline immunoglobulin region or in recombined and/or mutated forms thereof whether or not said antibodies are produced in human cells. The term "human antibody" also includes a human antibody engineered to take the form of a single chain FV fragment. The mutations may be processed via backmutation.

The term "backmutation" refers to a process in which some or all of the somatically mutated amino acids of a human antibody are replaced with the corresponding germline residues from a homologous germline antibody sequence. The heavy and light chain sequences of the human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmutation may occur at any stage of antibody optimization; preferably, backmutation occurs directly before or after the selective mutagenesis approach. More preferably, backmutation occurs directly before the selective mutagenesis approach.

The phrase "recombinant human antibody" includes human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described in the examples), antibodies isolated from an animal (e.g., a mouse) that is transgenic for human immunoglobulin genes (Taylor et al. 1992) or antibodies prepared, expressed, created or isolated by any other means that involves splicing of human immunoglobulin gene sequences to other DNA sequences. Such recombinant human antibodies have variable and constant regions derived from human germline immunoglobulin sequences (Kabat et al. 1992). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or backmutation or both.

An "isolated antibody" includes an antibody that is substantially free of other antibodies having different antigenic specificities (e.g., an isolated antibody that specifically binds AMA-1 is substantially free of antibodies that specifically binds not to AMA-1). Moreover, an isolated antibody may be substantially free of other cellular material and/or chemicals.

The term "inhibit" or "inhibiting" means neutralizing, antagonizing, prohibiting, preventing, restraining, slowing, disrupting, stopping, or reversing progression or severity of that which is being inhibited, e. g., including, but not limited to cell invasion, cell division, cell growing, multiplication, an activity, a disease or condition.

In an advantageous embodiment, the antibodies according to the present disclosure, or an antigen-binding portion thereof, inhibits the invasion of *Plasmodium falciparum* parasites into human red blood cells (erythrocytes). As mentioned above, the invasion of red blood cells is a key event in the infection of a subject with the malaria parasite.

A "invasion inhibiting antibody" includes an antibody whose binding to AMA-1 results in inhibition of the invasion of *Plasmodium* parasites, in particular of *Plasmodium falciparum* parasites into human red blood cells. This inhibition of the invasion of human red blood cells can be measured by one or more of several standard assays known in the art (see Example 5).

In an advantageous embodiment, the antibodies according to the present disclosure, or an antigen-binding portion thereof, further may inhibits the growth i.e. neutralizes the multiplication of *Plasmodium* parasites, in particular of *Plasmodium falciparum* parasites.

A "growth-inhibiting antibody" includes an antibody whose binding to AMA-1 results in inhibition of the growth of *Plasmodium* parasites, in particular of *Plasmodium falciparum* parasites.

In an advantageous embodiment, the isolated human antibodies according to the present disclosure, or antigen-binding portion thereof, inhibits the invasion of *Plasmodium* parasites, in particular of *Plasmodium falciparum* parasites into the erythrocyte and/or the growth of *Plasmodium* parasites, in particular of *Plasmodium falciparum* parasites within the erythrocyte in a range of 5% to 100%, preferably 10% to 90%, more preferably 20% to 80%, more preferably 30% to 70%, more preferably 40% to 60%.

In an advantageous embodiment, the isolated human antibodies according to the present disclosure, or antigen-binding portion thereof, inhibit the invasion of *Plasmodium* parasites, in particular of *Plasmodium falciparum* parasites into the erythrocyte and/or the growth of *Plasmodium* parasites, in particular of *Plasmodium falciparum* parasites within the erythrocyte of at least 10%, of at least 20%, of at least 30%, of at least 40%, of at least 50% and in particular of at least 60%. In particular, the isolated human antibodies according to the present disclosure, or antigen-binding portion thereof, inhibits the growth of *Plasmodium* parasites, in particular of *Plasmodium falciparum* parasites of at least 80, at least 85, at least 95%, and in particular of 100% (see FIG. 7). In a further embodiment, the described human antibodies inhibit the growth of the *Plasmodium falciparum* parasites at 50% ($IC_{50}$) at concentrations below 5 mg/ml, below 1 mg/ml, below 500 µg/ml, below 200 µg/ml and in particular below 100 µg/ml. Furthermore, in some advantageous embodiments the described human antibodies inhibit the growth of the *Plasmodium falciparum* parasites at 50% ($IC_{50}$) at concentrations above 0.05 mg/ml, 0.06, 0.07, 0.08, 0.09 and in particular above 0.1 mg/ml. The growth of all tested strains may be inhibited at 50% ($IC_{50}$) at concentrations above 0.1 mg/ml, 0.5 mg/ml, in particular with a concentration between 0.1 mg/ml and 1 mg/ml.

The term "epitope" as used herein refers to a region of a protein molecule to which an antibody can bind. An "immunogenic epitope" is defined as the part of a protein that elicits an antibody response when the whole protein is the immunogen, as for example described before by Geysen et al. (Geysen et al. 1984). An "antigen binding portion" of an antibody, as used herein, refers to a region of an antibody that interacts with or binds to an epitope to which the antibody binds when the antigen binding portion is comprised within an antibody. The antigen binding portion may exist outside the context of the full length antibody and still be considered to be an antigen binding portion of the antibody whether or not it still interacts with or binds to an epitope.

The term "modified form" or "variant" means that the antibody or an antigen-binding portion thereof has been modified but retains the same functional characteristics.

The term "fusion proteins" comprises an antibody, an antigen-binding portion or any variant thereof by covalently fusing additional amino-acid sequences at the C- and/or N-terminus. The source and composition of the additional amino-acid sequence is either natural from any living organisms or virus or unnatural. In particular, the fusion protein may be a "recombinant" polypeptide which is defined either by its method of production or its structure. In reference to its method of production, e. g., a product made by a process, the process involved uses of recombinant nucleic acid techniques. In reference to structure, recombinant polynucleotides or polypeptides contain sequences from different sources. In particular, it encompasses polypeptides made by generating a sequence comprising two or more fragments which are not naturally contiguous or operably linked to each other. Thus, for example, products made by transforming cells with any unnaturally occurring vector are encompassed.

The term "homologous polypeptide" according to the present disclosure comprises any antibody or antigen-binding portion thereof with a sequence identity of at least 70% or preferably at least 80%, 85%, 90%, 95%, 97% or 99% to the LCVRs, HCVRs or CDRs according to the present disclosure.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 3 either in one- or in three-letter code.

The phrase "contact position" includes an amino acid position of in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the 26 known solved structures of antibody-antigen complexes contacts the antigen, then that amino acid can be considered to occupy a contact position. Contact positions have a higher probability of being occupied by an amino acid which contact antigen than noncontact positions. Preferably a contact position is a CDR position which contains an amino acid that contacts antigen in greater than 3 of the 26 structures (greater than 11.5 percent). Most preferably a contact position is a CDR position which contains an amino acid that contacts antigen in greater than 8 of the 25 structures (greater than 32 percent).

The term "hypermutation position" includes an amino acid residue that occupies position in the CDR1, CDR2 or CDR3 region of the heavy chain variable region or the light chain variable region of an antibody that is considered to have a high frequency or probability for somatic hypermutation during in vivo affinity maturation of the antibody. "High frequency or probability for somatic hypermutation" includes frequencies or probabilities of a 5 to about 40 percent chance that the residue will undergo somatic hypermutation during in vivo affinity maturation of the antibody. It should be understood that all ranges within this stated range are also intended to be part of this invention, e.g., 5 to about 30 percent, e.g., 5 to about 15 percent, e.g., 15 to about 30 percent.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "modification" as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term "modifying", as used herein, includes changing one or more amino acids in the antibodies or antigen-binding portions thereof. The change can be produced by adding, substituting or deleting an amino acid at one or more positions. The change can be produced using known techniques, such as PCR mutagenesis.

TABLE 3

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |

TABLE 3-continued

Amino acid abbreviations

| Abbreviations | | Amino acid |
|---|---|---|
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone and Barton 1993; Taylor 1986). Conservative substitutions may be made, for example, according to Table 4 below which describes a generally accepted Venn diagram grouping of amino acids.

TABLE 4

Venn diagram grouping amino acids

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN (Dayhoff 1979), National Biomedical Research Foundation, Washington, D.C., which adapts the local homology algorithm of Smith and Waterman for peptide analysis (Smith and Waterman 1981). Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which was described before (Altschul et al. 1990). Software for performing BLAST analyses is publicly available through the National Center for Biotechnology Information. Likewise, computer programs for determining percent homology are also readily available.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

The term "isolated" when used in relation to a nucleic acid or protein (e. g. an antibody), refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature. Preferably, an "isolated antibody" is an antibody that is substantially free of other antibodies having different antigenic specificities.

The human antibodies or antigen-binding portion thereof according to the present disclosure can also be produced in phage display libraries (Hoogenboom and Winter 1992). The techniques of Cole, et al., and Boerner, et al., are also among those techniques available for the preparation of human monoclonal antibodies (Boerner et al. 1991; Reisfeld et al. 1985).

Recombinant human antibodies may also be subjected to in vitro mutagenesis (or, when an animal transgenic for human Ig sequences is used, in vivo somatic mutagenesis) and, thus, the amino acid sequences of the HCVR and LCVR regions of the recombinant antibodies are sequences that, while derived from those related to human germline HCVR and LCVR sequences, may not naturally exist within the human antibody germline repertoire in vivo.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell which comprises a recombinant vector of the invention may also be referred to as a "recombinant host cell". Preferably the host cell is bacterial, agrobacterial, plant or mammalian; if plant, it is preferably a *Nicotiana benthamiana* plant or BY2 cells thereof, if mammalian, it is preferably a CHO, COS, NSO or HEK 293 cell.

A wide variety of host expression systems can be used to express an antibody of the present disclosure including prokaryotic (bacterial) and eukaryotic expression systems (such as yeast, baculoviral, plant, mammalian and other animal cells, transgenic animals, and hybridoma cells), as well as phage display expression systems. An example of a suitable bacterial expression vector is pUCI 19 (Sfi), and a suitable eukaryotic expression vector is a modified pcDNA3.1 vector with a weakened DHFR selection system. Another example for a suitable eukaryotic expression vector is a modified pMS vector carrying a zeocin resistance and an IRES site (Stöcker et al. 2003). Another example for a suitable expression vector is the pTT vector system, carrying an improved CMV expression cassette as well as an oriP site for enhanced replication in HEK 293-6E cells (Durocher et al. 2002). An example of the plant expression vector is the pTRAkt, which is electroporated into agrobacteria and subsequently infiltrated into tobacco plants (Boes et al. 2011). Other antibody expression systems are also known in the art and are contemplated herein.

Furthermore, an EBV-transformed human lymphoblastoid B cell line may be used as an expression system or the antibodies or binding-portions thereof can be expressed in a cell-free protein synthesis system, for example derived from an E. coli extract.

Therefore, the present disclosure includes also methods of producing isolated antibodies or an antigen-binding portions thereof, wherein the methods comprise:

(a) providing a nucleic acid construct comprising a nucleic acid encoding the antibody or an antigen-binding portion thereof, (b) adding the nucleic acid construct to a cell-free lysate obtained from eukaryotic or procaryotic cells, and (c) isolating/purifying the isolated antibody or an antigen-binding portion thereof from the lysate, and optionally (d) isolating and/or purifying and/or processing of said antibody or an antigen-binding portion thereof.

An antibody or antigen-binding portion thereof according to the present disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell. Preferably, the recombinant antibodies are secreted into the medium in which the host cells are cultured, from which the antibodies can be recovered. Standard recombinant DNA methodologies are used to obtain antibody heavy and light chain genes, incorporate these genes into recombinant expression vectors, and introduce the vectors into host cells. Such standard recombinant DNA technologies are described before (Ausubel et al. 1989; Sambrook et al. 1989) and in U.S. Pat. No. 4,816,397 by Boss, et al. (Boss et al. 1984).

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art (Kabat et al. 1992). DNA fragments encompassing these regions can be obtained by standard PCR amplification. The heavy chain constant region can be an IgGl, IgG2, IgG3, IgG4, IgA, IgE, IgM or IgD constant region and any allotypic variant thereof as described in Kabat (supra), but most preferably is an IgG4 or an IgGl constant region. Alternatively, the antigen binding portion can be a Fab fragment, a F(ab')$_2$ fragment, or a single chain Fv fragment (scFv). For a Fab fragment heavy chain gene, the HCVR-encoding DNA can be operably linked to another DNA molecule encoding only a heavy chain CH1 constant region.

An isolated DNA encoding a LCVR region can be converted to a full-length light chain gene (as well as a Fab light chain gene) by operably linking the LCVR-encoding DNA to another DNA molecule encoding a light chain constant region, CL. The sequences of human light chain constant region genes are known in the art (Kabat et al. 1992). DNA fragments encompassing these regions can be obtained by standard PCR amplification. The light chain constant region can be a kappa or lambda constant region.

To create a scFv gene, the HCVR- and LCVR-encoding DNA fragments are operably linked to another fragment encoding a flexible linker, e. g., encoding the amino acid sequence (Gly4-Ser) 3, such that the HCVR and LCVR sequences can be expressed as a contiguous single-chain protein, with the LCVR and HCVR regions joined by the flexible linker. Examples were published by Bird et al., Huston, et al. and McCafferty, et al. (Bird et al. 1988; Huston et al. 1988; McCafferty et al. 1990).

To express an antibody or antigen-binding portion thereof of the disclosure, a DNA encoding a partial or full-length light and/or heavy chain, obtained as described above, may be inserted into an expression vector such that the gene is operably linked to transcriptional and translational control sequences. In this context, the term "operably linked" means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the antibody light and/or heavy chain from a host cell. The human antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene (s), a recombinant expression vector of the invention carries regulatory sequences that control the expression of the antibody chain gene (s) in a host cell. The term "regulatory sequence" is intended to include promoters, enhancers and other expression control elements (e. g. polyadenylation signals), as needed, that control the transcription or translation of the antibody chain gene (s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e. g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e. g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced.

Further examples for selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NSO) for selection/amplification.

For expression of the light and/or heavy chains, the expression vector (s) encoding the heavy and/or light chains is transfected into a host cell by standard techniques e. g, electroporation, calcium phosphate precipitation, DEAE-dextran transfection and the like.

Although it is theoretically possible to express the antibodies or the antibody fragments of the present disclosure in either prokaryotic or eukaryotic host cells, preferably eukaryotic cells, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO cells) (including DHFR-CHO cells (Urlaub and Chasin 1980)) used with a DHFR selectable marker, e. g., as described before (Kaufman and Sharp 1982), NSO myeloma cells, COS cells, HEK 293 and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e. g., Fab fragments or scFv molecules. It will be understood that variations on the above procedure are within the scope of the present disclosure. For example, it may be desirable to transfect a host cell with DNA encoding either the light chain or the heavy chain (but not both) of an antibody of this disclosure.

Plant cells can also be modified to create transgenic plants that express the antibody, or an antigen-binding portion thereof, of the present disclosure.

Further aspects of the disclosure relate to: a method of expressing in a host cell a antibody or a binding-portion thereof from a nucleic acid molecule as described herein; a host cell capable of expressing a polypeptide as described herein in appropriate culture conditions for producing said polypeptide; a method of producing a fusion protein comprising culturing such a host cell under appropriate conditions, which method may further comprise isolating said fusion protein from the cell culture, and which method may further comprise admixing the isolated fusion protein with a suitable further component (which may, for example, be another protein or an excipient or carrier).

As discussed above, in accordance with the present disclosure, the polypeptides may be produced in any desirable system vector constructs and expression systems are well known in the art and may be adapted to incorporate use of polypeptides provided herein. For example, transgenic plant production is known and generation of constructs and plant production maybe adapted according to known techniques in the art.

In view of the foregoing, another embodiment of the disclosure pertains to nucleic acids, vectors, and host cell compositions that can be used for recombinant expression of the antibodies and antibody portions of the disclosure. Preferably, the disclosure provides isolated nucleic acids that comprise a region encoding one or more CDRs of huMAb-anti-AMA-1.1 and even more preferably those CDRs exist in the expressed protein (e. g. antibody or antigen binding portion thereof) at the same CDR site within the antibody structure as they exist in antibody huMAb-anti-AMA-1.1 (see Table 1).

Further embodiments pertain to complexes which can be regarded as heterologous complexes comprising at least two domains, i.e., one effector domain and one binding domain.

In advantageous embodiments, the present disclosure pertains to complexes which are formed from at least one antibody of the present disclosure or an antigen-binding portion thereof as a specific binding domain and at least one effector domain, wherein the antibody or antigen-binding portion thereof has a binding activity to AMA-1, in particular to domain I of AMA-1 (SEQ ID NO: 16) of *Plasmodium falciparum*, and the effector domain carries a cytotoxic reagent as an effector function. In particular the complex comprises a fusion protein including the binding domain and the effector domain.

In certain embodiments, the binding domain as cell targeting moieties for use in the current disclosure is recombinant antibodies or antigen-binding portion thereof according to the present disclosure. The antigen-binding portion of the antibodies according to the present disclosure may be comprised in monoclonal antibodies, single chain antibodies, humanized antibodies, minibodies, diabodies, tribodies as well as antibody fragments, such as Fab', Fab, F(ab')$_2$ or single domain antibodies.

In some embodiments, the effector domain induces apoptosis of *Plasmodium falciparum*. Alternatively, other molecules capable of eliciting the desired effector functions or anti-parasitic effects may be coupled to the antigen-binding region of the antibodies, e. g. enzymes with anti-parasitic effects. For example, the use of such antibodies may confer target selectivity to an otherwise toxic drug or substance.

Accordingly, in a further aspect the present disclosure provides an isolated nucleic acid molecule comprising a nucleic acid sequence encoding a recombinant human antibody or an antigen-binding portion thereof. Such a nucleic acid molecule may be in the form of a recombinant and preferably replicable vector.

Such vector may be any plasmid, cosmid, or phage in double or single stranded linear or circular form which may or may not be self-transmissible or mobilizable, and which can transform prokaryotic or eukaryotic host either by integration into the cellular genome or exist extrachromosomally (e. g. autonomous replicating plasmid with an origin of replication). Any suitable host may be used, including bacteria, e. g. archaebacteria, plants, plant cell, fungi.

Generally speaking, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference. Preferred vectors include the plasmids pMS, pTT and pTRAkt (Boes et al. 2011; Durocher et al. 2002; Stöcker et al. 2003).

It is preferred that the antibody is secreted to the media by the cell from which it is expressed.

Further aspects of the invention relate to: a method of expressing in a host cell an antibody or an antigen-binding portion thereof as described herein from a nucleic acid molecule described herein; a host cell capable of expressing an antibody as described herein in appropriate culture conditions for producing said antibody; a method of producing an antibody comprising culturing such a host cell under appropriate conditions, which method may further comprise isolating said antibody from the cell culture, and which method may further comprise admixing the isolated antibody with a suitable further component (which may, for example, be another antibody or an excipient or carrier).

Mammalian cells may be transfected by any suitable technique such as lipofection. Alternatively, standard calcium phosphate transfection or electroporation may be used, which is well understood by the skilled person. The recombinant antibodies produced from these expression systems and nucleic acid molecules of the disclosure are preferably provided in a substantially pure or homogeneous form.

Recombinant antibodies may be purified by any suitable method affinity chromatography followed using mAB select or Protein A sepharose. This may optionally be followed by a gel filtration step, e. g. using Superdex200.

In yet a further aspect, the disclosure relates to a nucleic acid molecule and to the use of a nucleic acid molecule selected from the group consisting of a) a nucleic acid molecule encoding an antibody or an antigen-binding portion thereof according to the present disclosure;

b) a nucleic acid molecule encoding for a modified form of an antibody or an antigen-binding portion thereof according to the present disclosure, preferably in which one or more amino acid residues are conservatively substituted;

c) a nucleic acid molecule that is a fraction, variant, homologue, derivative, or fragment of the nucleic acid molecule presented as SEQ ID NO:7, SEQ ID NO:8, SEQ ID NO:9, SEQ ID NO:10 SEQ ID NO:11 and/or SEQ ID NO:12.

d) a nucleic acid molecule encoding fragments of the isolated antibody or antigen-binding portion thereof according to the present disclosure e) a nucleic acid molecule that is capable of hybridizing to any of the nucleic acid molecules of a)-d) under stringent conditions f) a nucleic acid molecule that is capable of hybridizing to the complement of any of the nucleic acid molecules of a)-e) under stringent conditions g) a nucleic acid molecule having a sequence identity of at least 80% with any of the nucleic acid molecules of a)-f) and encoding for an antibody of the present disclosure or an antigen-binding portion thereof, h) a nucleic acid molecule having a sequence identity of at least 85% with any of the nucleic acid molecules of a)-f) and encoding an antibody of the present disclosure or an antigen-binding portion thereof, i) or a complement of any of the nucleic acid molecules of a)-h).

A nucleotide or nucleic acid is considered to hybridize to one of the above nucleotides if it is capable of hybridizing under conditions of medium stringency, more preferably high stringency, even more preferably under very high stringency conditions.

The nucleic acid molecule of the present disclosure may comprise nucleotide sequences that encode for SEQ ID NO:7, SEQ ID NO:8, SEQ ID NO:9, SEQ ID NO:10 SEQ ID NO:11 and/or SEQ ID NO:12, listed in Table 5.

Table 5 shows the nucleic acid sequences of complementarity-determining regions 1-3 (CDR 1-3) of the antibody heavy and light chains.

TABLE 5

Nucleic Acid Sequences of LCVR and HCVR of AMA-1-binding antibody huMAb-anti-AMA1.1

| SEQ ID # | CDR # | Nucleic Acid Sequence according to Kabat definition (Martin 1020) |
|---|---|---|
| SEQ ID NO: 7 | CDR1 (VL) | CGGGCCAGTCAGAGTATTACTACCT GGTGGCC |
| SEQ ID NO: 8 | CDR2 (VL) | AAGGCGTCTATTTTAGAGACT |
| SEQ ID NO: 9 | CDR3 (VL) | CAACAGTATAGTACTCACCTATTCA CT |
| SEQ ID NO: 10 | CDR1 (VH) | AGTACTGTGTTCTACTGGGGC |
| SEQ ID NO: 11 | CDR2 (VH) | AGTATCTATTATAGTGGTAGCACGT ACTACAATGAGGCCCTCAAGAGC |
| SEQ ID NO: 12 | CDR3 (VH) | GGGGCGATTAATTTTGGGGGATATT CGGGCCCCGGGACCTTCTATTTTGA CATT |

Some embodiments relates to an isolated nucleic acid molecule encoding an antibody or an antigen-binding portion or parts thereof according to the present disclosure. Nucleic acid sequences encoding parts or fragments of the antibody or antigen-binding portion thereof like the variable region of the antibody comprising the variable light chain variable region and the heavy chain variable region may be located at a single nucleic molecule like a vector. In some embodiments parts or fragments of the antibody or antigen-binding portion thereof may be located at different nucleic acid molecules like different vectors.

In particular, the nucleic acid molecule comprises an nucleic acid sequence selected from the group consisting of SEQ ID NO:7, SEQ ID NO:8, SEQ ID NO:9, SEQ ID NO:10, SEQ ID NO:11 and SEQ ID NO:12. Therefore, the nucleic acid molecule encodes an antibody variable region or a part thereof, wherein the light chain variable region of said variable region comprises CDR1 of SEQ ID NO:1, CDR2 of SEQ ID NO:2 and CDR3 of SEQ ID NO:3, and the heavy chain variable region comprises CDR1 of SEQ ID NO:4, CDR2 of SEQ ID NO:5 and CDR3 of SEQ ID NO:6.

In some embodiments, the nucleic acid molecule comprises SEQ ID NO:7, SEQ ID NO:8 and SEQ ID NO:9 and/or the SEQ ID NO:10, SEQ ID NO:11 and SEQ ID NO:12.

In particular, the disclosure provides a plasmid, a vector system or a vector combination comprising a nucleic acid sequence encoding a polypeptide as described herein or a homologue or derivative thereof.

The antibodies or the antigen-binding portion thereof as well as the complexes of the present disclosure can be used with a "pharmaceutically acceptable carrier" which includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human.

Except insofar as any conventional carrier is incompatible with the active ingredient, its use in the therapeutic or pharmaceutical compositions is contemplated.

The actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In advantageous embodiments, antibodies or the antigen-binding portion thereof as well as the complexes according to the disclosure are used for preparing a medicament for preventing or treating malaria, in particular Malaria tropica.

Figure 1:
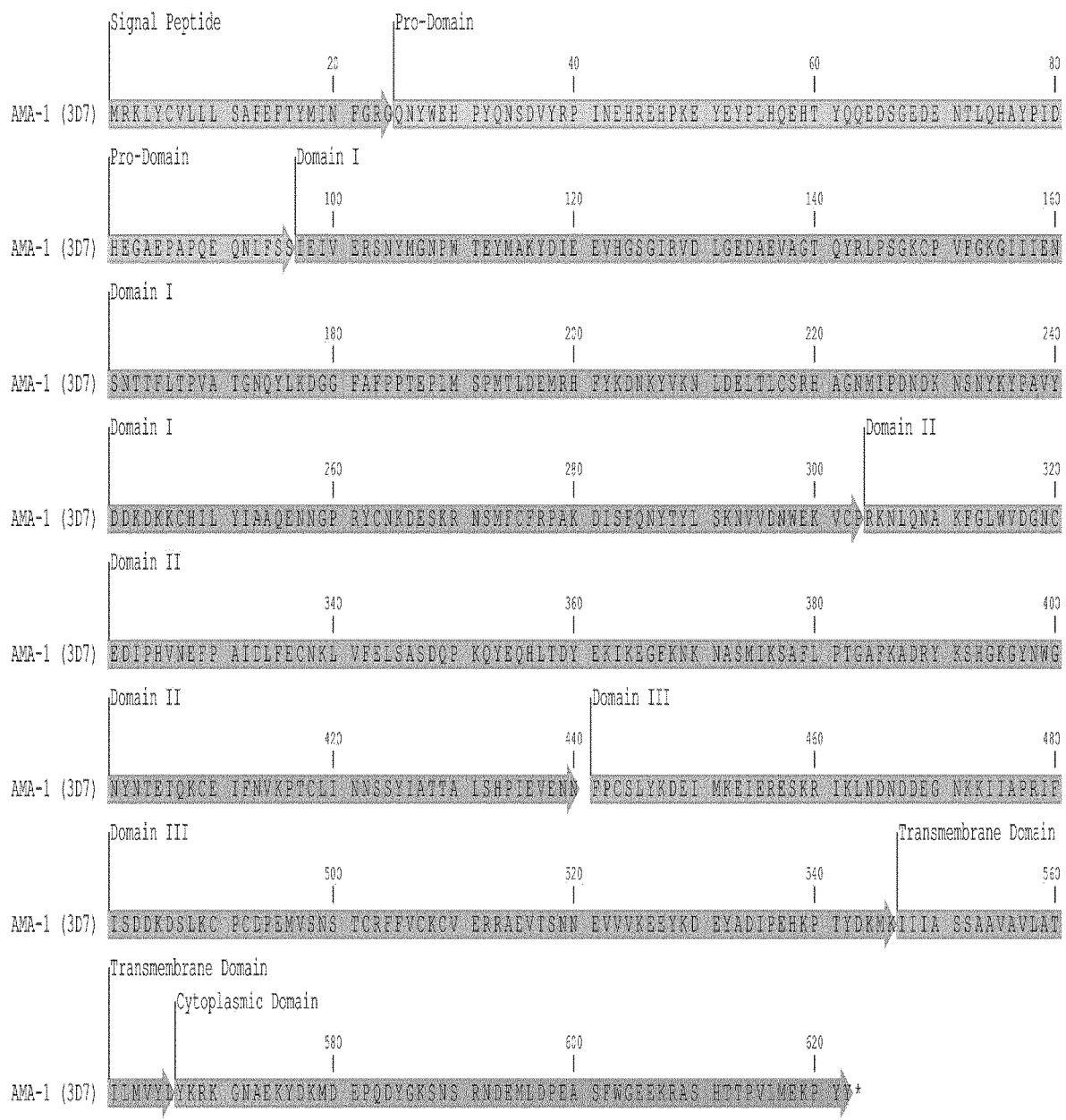
FIG. 1 shows the annotated amino acid sequence of the apical membrane antigen 1 (AMA-1) (SEQ ID NO: 15).

FIG. 1 shows the sequence of the apical membrane antigen 1 (AMA-1). The domains I, II and II are marked by boxes.

Figure 2:
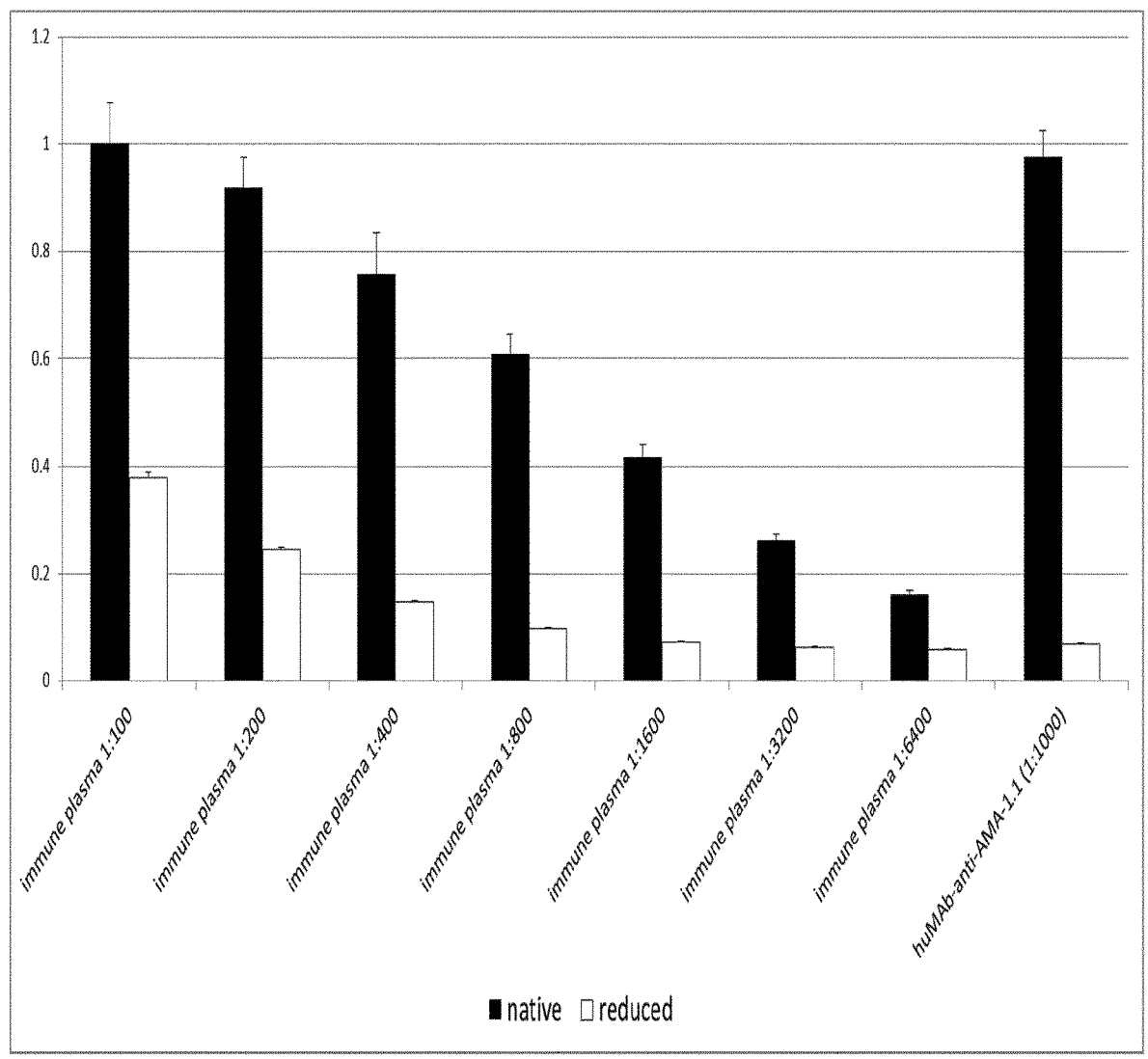
FIG. 2 is a diagram showing the results from the ELISA assay for the binding activity and specificity of the antibody huMAb-anti-AMA-1.1 to recombinant AMA-1.

FIG. 2 shows the results of the ELISA assay, in particular the reactivity of the huMAb-anti-AMA-1.1 antibody comprising SEQ ID NO: 1 to SEQ ID NO: 6 to the domain I of the apical membrane antigen 1 (AMA-1) (SEQ ID NO: 16). Recombinant AMA-1 produced in *Pichia pastoris* in its native form as well as in its reduced (denatured) form was incubated overnight on ELISA plates. Reactivities of plasma from semi-immune donors, as well as recombinant human antibody huMAb-anti-AMA-1.1 from crude plant extract was quantified. The activities are shown as relative reactivities towards the reactivity of semi-immune plasma against the native protein.

Figure 3:
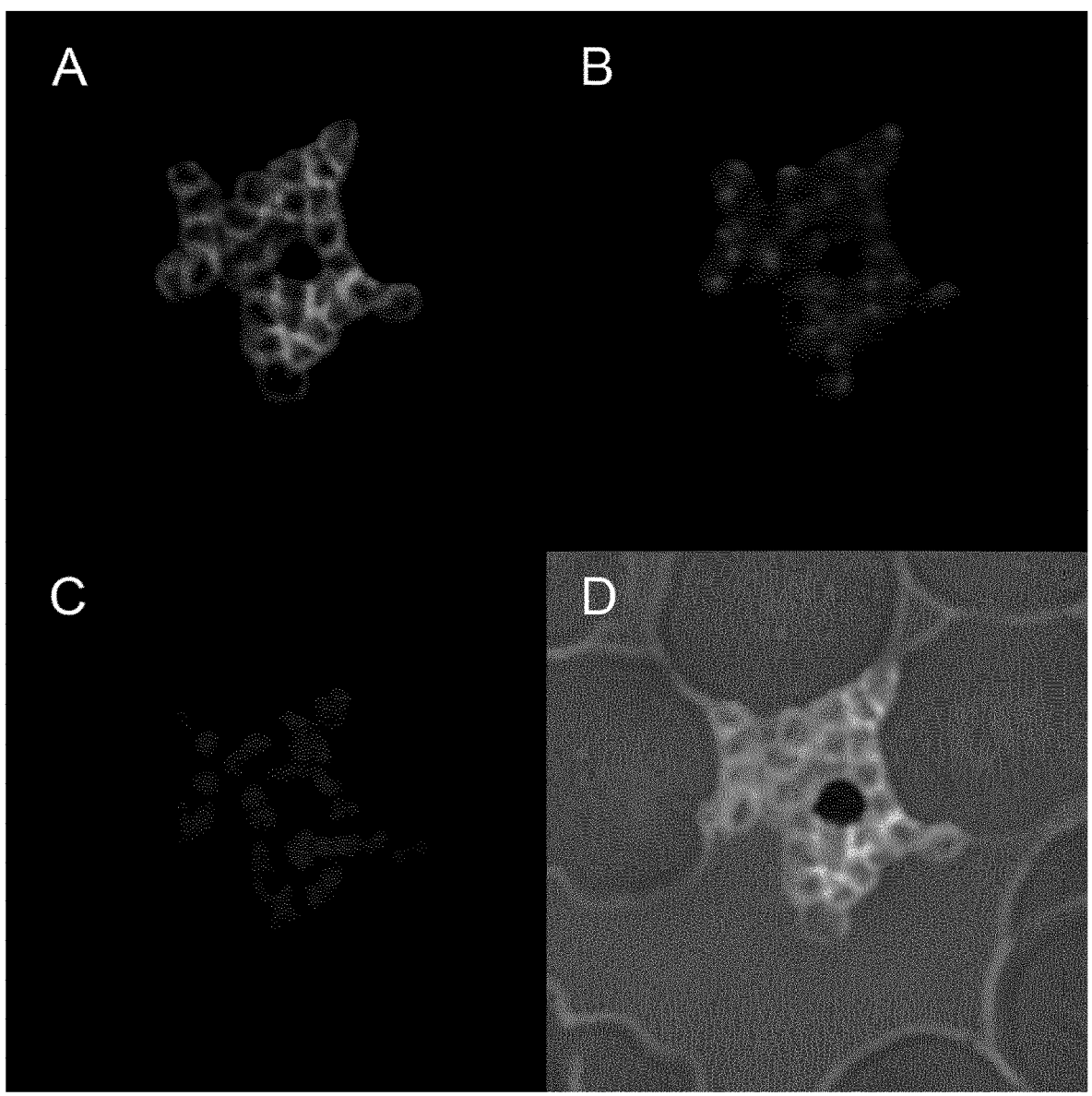
FIG. 3 shows the binding of the recombinant antibody huMAb-anti-AMA-1.1 to *Plasmodium falciparum* schizonts by immunofluorescence assay (IFA).

FIG. 3 shows the binding of recombinant antibody huMAb-anti-AMA1.1 by immunofluorescence assay (IFA). Mature schizonts from the parasite strain 3D7 were fixed on slides and co-stained with murine anti-MSP4 antibody 2.44 followed by a goat anti mouse Alexa 488 (A) and recombinant human anti AMA-1 antibody huMAb-anti-AMA1.1 followed by a goat anti-human Cy3 (B). Nuclei were costained using the DNA stain Hoechst 33342 (C) The overlay of the three images including the brightfield image is shown in D. Images were taken on a Leica TCS SP8 confocal microscope. Secondary antibodies alone do not show any reaction (data not shown).

FIG. 4 shows the complete heavy and light chain variable regions with the framework regions and the complementarity determining regions highlighted. Sequences were analyzed according to the Kabat definition (FIG. 4A) and using IMGT/V-QUEST (FIG. 4B).

Figure 5:
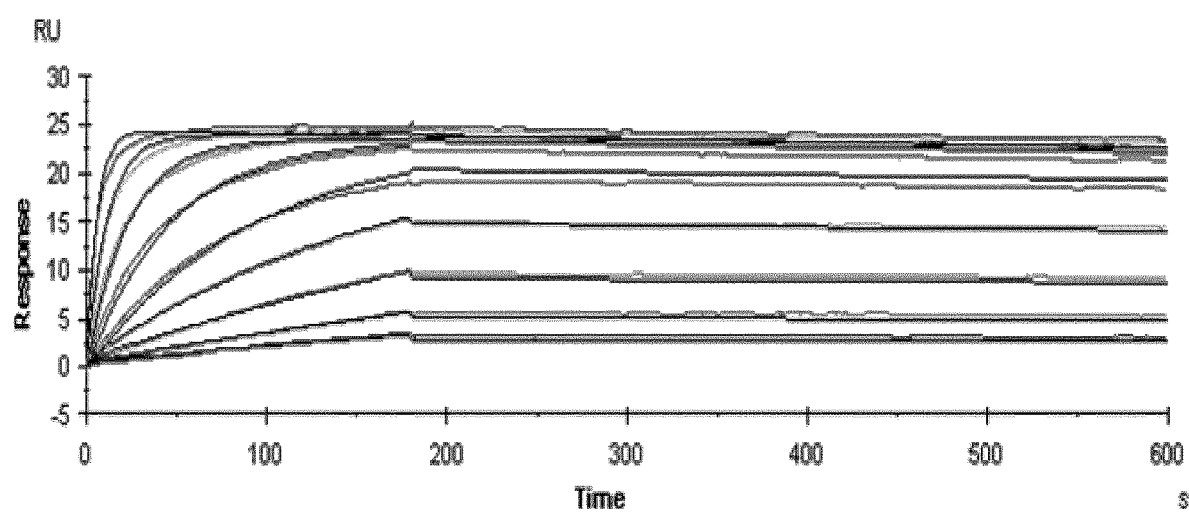
FIG. 5 shows the results of the KD-value determination by surface plasmon resonance (SPR).

FIG. 5 shows the results of the KD-value determination by surface plasmon resonance (SPR), as described in example 3.

Figure 6:
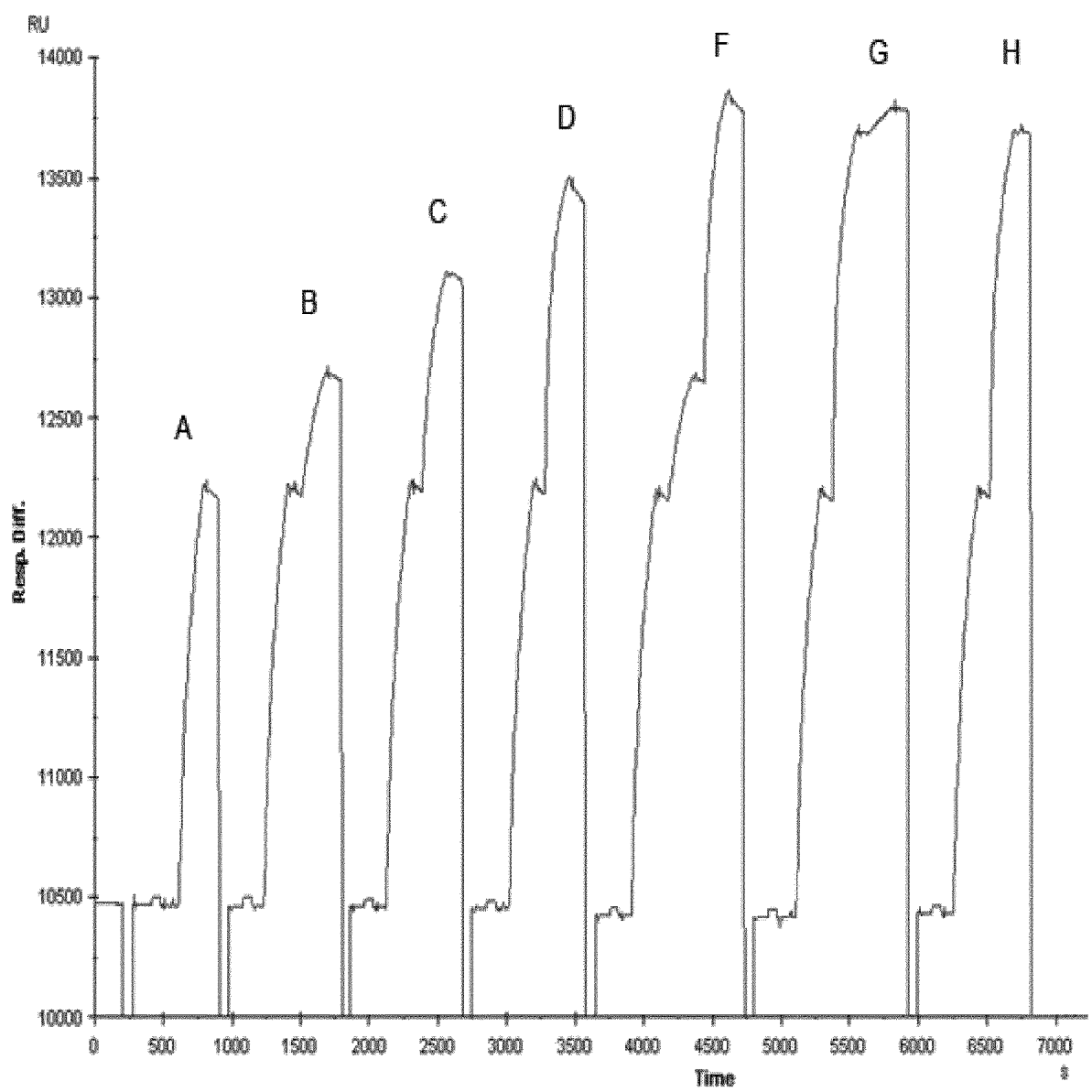
FIG. 6 shows the pairwise epitope binding assay performed by competitive SPR analysis.

FIG. 6 shows the pairwise epitope antibody binding assay performed by competitive SPR analysis, as described in example 3. The antibody 1 D7 was immobilized on the surface of the chip. Subsequently, the antigen AMA-1 was bound (A). In B-D, the individual binding of huMAb-anti-AMA1.1 (1 µg/ml), the mAb 1F9 (10 µg/ml) and the mAb 4G2 (1 µg/ml) on the immobilized AMA-1 are shown, respectively. Subsequently, pairwise antibody binding assays were performed. Tested were the pairwise binding of huMAb-anti-AMA1.1 (1 µg/ml) vs. mAb 4G2 (1 µg/ml) (F), and the pairwise binding activity of huMAb-anti-AMA1.1 (10 µg/ml) and mAb 1F9 (10 µg/ml) (G). In (H), binding of huMAb-anti-AMA1.1 alone to AMA-1 at a concentration of 10 µg/ml is shown.

FIG. 7 shows the results of the growth inhibition assay (GIA) against the parasite strains 3D7 using the antibody huMAb-anti-AMA1.1 in comparison to the antibodies of rodent origin 4G2 (rat) and 1F9 (murine), as described in example 5.

FIG. 8 shows the results of the growth inhibition assay (GIA) against the parasite strains 3D7, HB3, K1 and FCR3, as described in example 5.

Figure 9:
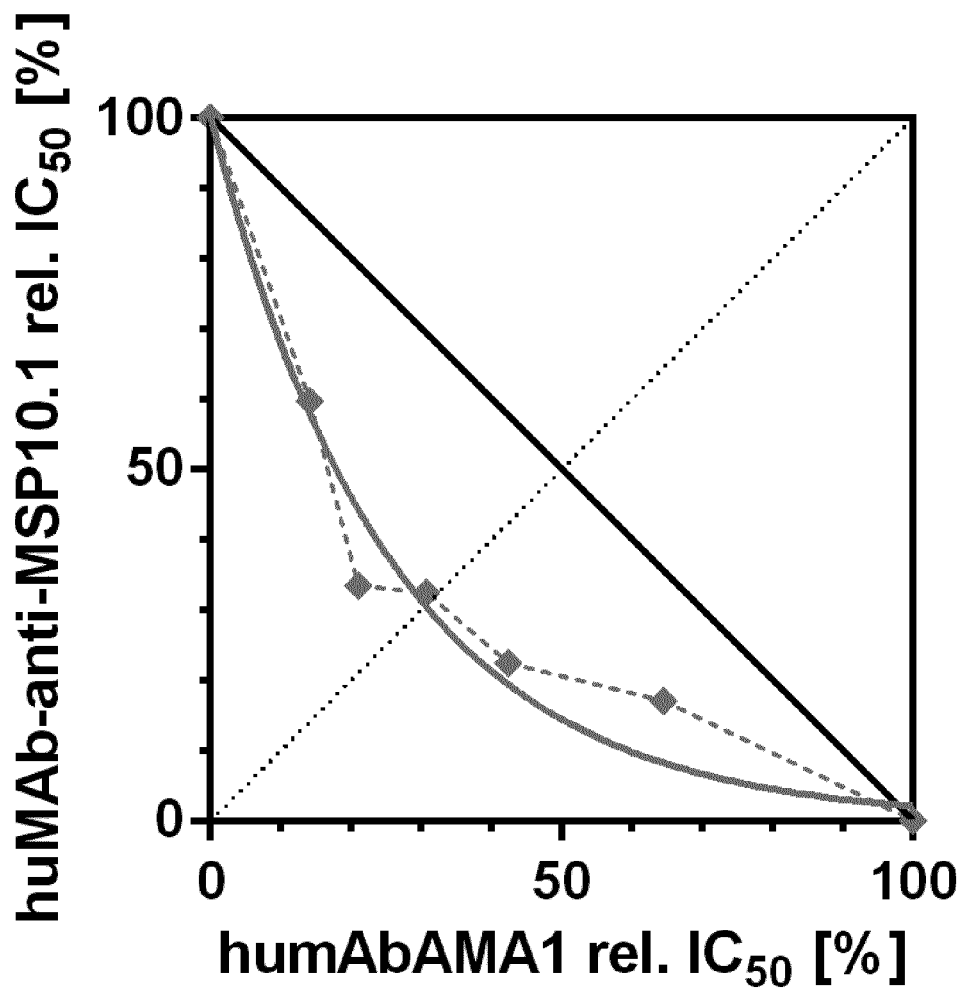

FIG. 9 shows the results of the growth inhibition assay combining the antibody huMAb-anti-AMA-1.1 with the antibody huMAb-anti-MSP10.1, as described in example 6.

The following methods and examples are offered for illustrative purposes only, and are not intended to limit the scope of the present disclosure in any way.

METHODS AND EXAMPLES

In the following examples, materials and methods of the present disclosure are provided including the determination of binding and inhibiting properties of the antibodies according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1

Memory B Cell Immortalization and V Gene Amplification

From one Ghanaian semi-immune adult, 50 ml of blood were withdrawn and PBMCs isolated by density gradient centrifugation. PBMCs were cryopreserved in FCS containing 10% DMSO and kept at −150° C. until usage.

Memory B cells were immortalized by Epstein Barr Virus (EBV) transformation according to standard procedures (Fraussen et al. 2010). Once B cell cultures were stably growing, cells were maintained in RPMI containing 10% FCS, 10 mM Hepes and 1 mM sodium pyruvate. Supernatants were collected and assayed for specificity against the antigen AMA-1. Corresponding EBV-transformed antibody-producing B cells were collected. Using the Cells-Direct Kit (Invitrogen), cDNA was directly prepared from 100-1000 cells. V genes were amplified from cDNA by nested PCR using primers described before (Tiller et al. 2008).

Amplified sequences were cloned into the plant expression vector pTRAkt expression vector system according to standard procedures containing the heavy chain constant domain allotype IgG1m17,1 and a kappa chain constant domain for the light chain. Cloned heavy and light chain sequences were sequenced. Obtained sequences were analyzed using IMGT/V-QUEST (VQUEry and STandardization) (Brochet et al. 2008). The V-QUEST tool from the International Immunogenetics Information System aligns query antibody sequences to the internal antibody sequences of germline sequences. The tool also assigns the regions of the antibody corresponding to framework regions and the cluster of differentiation regions one to three. The CDR regions defining the huMAb-anti-AMA-1.1 were allocated according to the results obtained from IMGT/V-QUEST.

From the Ghanaian donor, $1.1 \times 10^7$ viable PBMC were recovered. The viability after thawing of the cells was 60%.

During the sorting process, 14,000 antigen positive B-cells were isolated. After transformation of the B memory cells with EBV, cells were growing in clusters after 3 weeks and subcultured. Out of 149 wells which were sorted to be *P. falciparum* antigen specific, one was reacting against the AMA-1 according to the ELISA result of the tested supernatant. FIG. 1 shows the sequence of AMA-1.

After V-gene rescue, IMGT/V-QUEST analysis revealed the heavy chain variable region sequence to belong to family IGHV4 (identity 89%) and the light chain variable region belong to the family IGKV2 (identity 98%). Therefore, all three CDR have undergone strong affinity maturation processes in vivo. The complete variable domain from the antibody is represented in FIG. 4. The CDR regions 1-3 from both the heavy and light chains are underlined.

Example 2

Expression of Recombinant Antibodies in *Nicotiana benthamiana*

The recombinant expression of the antibodies was performed in *Nicotiana benthamiana* as described before (Boes et al. 2011). Basically, pTRAkt vectors containing either a light chain or a heavy chain antibody sequence were electroporated into *Agrobacterium tumefaciens* strain GV3101 (pMP90RK). Successful transformation was controlled by colony-PCR using the corresponding vector primers PS5 (ATCCTTCGCAAGACCCTTCCTCT) and PS3 (AGAGA-GAGATAGATTTGTAGAGA). Positive clones were picked and grown in YEB medium containing kanamycin (25 µg/ml) and carbenicillin (50 µg/ml) in increasing medium volume, maintaining an approximate OD of 2-4. When a volume of 1 liter was reached, agrobacteria were diluted in infiltration medium (final concentration 2 g/l glucose, 50 g/l sucrose and 0.5 g/l Ferty Mega 2, pH5.6) containing 100 µM Acetosyringon to a final OD of 1 and incubated for 1 hour. For optimal expression, agrobacteria expressing the silencing suppressor p19 were mixed at a ratio of 1:4 to the agrobacterium mixture. Subsequently, whole *Nicotiana benthamiana* plants were infiltrated by vacuum infiltration for 5 minutes. Infiltrated plants were kept for 5 days at room temperature in a humidified chamber. After the incubation period, whole plant protein was extracted by mixing in 2 volumes PBS in a blender for 1 minute. Plant debris was eliminated by centrifugation before antibodies were purified on a Mab-Select™ column (GE Healthcare) according to the manufactures instructions. After elution, antibodies were dialyzed against PBS and stored in aliquots at 4° C. and −20° C.

As mentioned above, the huMAb-anti-AMA-1.1 antibodies were expressed in *N. benthamiana* as full-length antibodies and subsequently purified. The yield of the expressed antibody typically varies between 50 and 200 mg per kg plant material. Purity and structural integrity of the antibody constructs was confirmed by SDS-PAGE under reducing and non-reducing conditions (data not shown).

Example 3

Determination of Antibody Specificity

Antibody specificity was estimated in a standard ELISA procedure. In short, the recombinantly produced AMA-1 from 3D7, produced in Pichia pastoris was coated overnight at 4° C. at a concentration of 1 µg/ml. Additionally, to control whether the antibody is binding a linear or conformational epitope, the antigen was reduced using 5 mM DTT (56° C., 45 min) and alkylated with 14 mM iodacetamide (RT, 30 min) and finally quenched using 5 mM DTT before coating. After a blocking step with PBS/1% BSA for 1 h at RT, the primary antibodies or human plasma was added at indicated dilutions and incubated for 1 hour at RT. After 3 washing steps using PBS/0.1% Tween20, the secondary goat anti-human IgG-alkaline phosphatase H+L specific, Promega (1:5000 in PBS) was added and also incubated for 1 h at RT. After a final washing step (3× 1 minute in PBS/1% Tween), the binding antibodies were visualized using pNPP (Sigma, N2765). Reactivities were quantified using a Biotek Epoch Spectrophotometer at a wavelength of 405 nm.

The isolated huMAb-anti-AMA-1.1 antibody presented here shows high binding specificity to the native target antigen AMA-1 (FIG. 2). In contrast to this, the antibody is not binding to the reduced/alkylated antigen. Thus, the reaction of the antibody could be determined to be specific for conformational epitopes the AMA-1 antigen (FIG. 2).

Binding assays were performed on a Biacore T200 instrument at 25° C. using a protein-A capture assay and HBS-EP as running buffer (Rosenberg et al. 2013). All antibodies were diluted into running buffer to yield equivalent capture levels. The injection time was set to 180 s and dissociation was recorded for 600 s. The protein-A surface was regenerated by a 30 s pulse with 30 mM HCl. For the antibody buffer injections were used for double referencing. Values for the $K_D$ of the antibody were calculated according to the curve-fitting methodology for a simple binding model (1:1 Langmuir). The individual measurements are shown in FIG. 5. The results of the affinity measurements are summarized in Table 6.

TABLE 6

Results of the affinity determination by SPR analysis

| Antibody | $K_a$ [M$^{-1}$ s$^{-1}$] | $K_d$ [s$^{-1}$] | $K_D$ [M] |
| --- | --- | --- | --- |
| huMAb-anti-AMA-1.1 | $6.98 \times 10^5$ | $1.31 \times 10^{-4}$ | $1.88 \times 10^{-10}$ |

In order to approximate the binding domain of the antibody huMAb-anti-AMA-1.1, a pairwise antibody binding assay was performed using three antibodies (1 D7, 4G2 and 1F9) with published binding epitopes. First, the antibody 1D7 was immobilized on the CM5-S-Series sensor chips. In a second step, the diluted AMA-1 was bound to the antibody for 180 seconds. As third step, either of the antibodies 4G2, 1F9 or huMAb-anti-AMA-1.1 was injected to control direct binding. After each of these individual antibody binding assays, the protein-A surface was regenerated by a 30 s pulse with 30 mM HCl.

For determination of potential epitope overlap, after binding of AMA-1, the antibody huMAb-anti-AMA-1.1 was injected into the system. Subsequently, antibodies 4G2 or 1F9 were injected, to control for competitive binding to similar epitopes as huMAb-anti-AMA-1.1.

The results of the experiments are summarized in FIG. 6. The antibodies 1F9, 4G2 and huMAb-anti-AMA-1.1 bound to the AMA-1 which was immobilized by the antibody 1 D7. This shows that no competitive binding occurred between any of the tested antibodies and the antibody 1D7. When the antibody huMAb-anti-AMA-1.1 was bound first, the antibody 4G2 could still bind to the AMA-1. In contrast to this, the antibody 1F9 binding to AMA-1 was reduced (by >90%), if huMAb-anti-AMA-1.1 was immobilized on the antigen. This indicates that the epitopes of both antibodies overlap or are at least in close proximity.

Example 4

Immunofluorescence Microscopy

Immunofluorescence Assay (IFA) was performed as described before (Roestenberg et al. 2008). *Plasmodium falciparum* parasites were washed thrice in RPMI+25 mM Hepes, resuspended in foetal calf serum (FCS), smeared on a slide and fixed at −20° C. in 100% methanol. Primary antibodies huMAb-anti-AMA-1.1 and monoclonal murine anti-MSP4 antibody 2.44 were incubated for 1 h at RT at a concentration of 25 µg/ml in PBS/1% FCS in a humid chamber. Subsequently, slides were washed 4× with PBS. Secondary Goat-anti human IgG-Alexa647 (Dianova, #109-605-003) and Goat-anti rabbit IgG-Alexa488 (Dianova, #111-545-003) were incubated at a dilution of 1:100 in PBS/1% FCS for 1 hour at RT. After a final washing step, slides were sealed using Vectashield Mounting Medium and subsequently analyzed using a Leica TCS SP8 confocal microscope.

AMA-1 is localized at the polar cap (micronemes) and the surface of merozoites In the immunofluorescence assay, the huMAb-anti-AMA-1.1 strongly stains a region at the apical end. In addition a dim staining is detectable on the surface of merozoites. In the IFA, the antibody huMAb-anti-AMA-1.1 staining co-localizes in part with the surface staining of the murine MSP4 antibody (see FIG. 3).

Example 5

Growth-Inhibition Assay (GIA)

Antibodies to be tested were purified using Protein A columns. The eluate was filter sterilized. Subsequently, the antibodies were concentrated and the buffer exchanged to RPMI containing 25% Hepes. The concentrations were estimated by Bradford Assay against an antibody standard.

The growth inhibitory potential against *plasmodium* parasites was performed using a standardized protocol. The *Plasmodium falciparum* parasite strains 3D7A, HB3, FCR3 and K1 (provided by MR4) were maintained in culture at parasitemias below 5% at a haematocrit of 4% in RPMI medium supplemented with 10% Albumax II (Invitrogen), 25 mM Hepes, 12 µg/ml gentamicin and 100 µM hypoxanthine at 37° C. and 5% $CO_2$, 5% $O_2$ and 90% $N_2$. The cultures were maintained in a daily routine and parasitemia estimated by Giemsa staining. The erythrocytes used in the assay were mixed from 15 malaria-naïve blood donors and not older than 3 weeks. The erythrocytes were stored in SAG-Mannitol at 4° C. The parasites were synchronized by 10% Sorbitol treatment within a time window of 1-16 hours post invasion. For the assay, only highly synchronous cultures 36 to 40 hours post invasion were used.

Parasites and fresh RBCs and antibodies were mixed in a 96-well plate appropriately in order to have a final parasitemia of 0.1% and a final hematocrit of 2%. For the background control, only RBCs without parasites were kept in culture under the same conditions as the parasites. A growth control for the monitoring the parasite growth was performed by culturing the *Plasmodium falciparum* parasite without additions. All samples were measured in triplicates. As negative control, malaria-naïve rabbit and human plasma were derived purified antibodies were tested. For positive control of complete invasion inhibition, EDTA (4 mM final concentration) and BG98 rabbit anti-AMA-1 polyclonal antibodies were used. Antibodies to be tested were the recombinant huMAb-anti-AMA-1.1.

The plates were incubated at 37° C., 95% humidity, 5% $CO_2$, 5% $O_2$ and 90% $N_2$ for 40 to 44 hours. At harvest, wells were washed once with cold PBS and frozen down. Parasite growth was estimated by a Malstat™ assay (Makler et al. 1993). Absorbance was measured after 30 minutes at a wavelength of 655 nm using a spectrophotometer. Inhibitory capacity was estimated by the following formula:

$$\% \text{ inhibition} = 100\% - \frac{(A655\ IgG\ \text{sample} - A655\ RBC\ \text{control})}{(A655\ Schizont\ \text{control} - A655\ RBC\ \text{control})} * 100\%$$

In order to test the inhibitory capacity of the huMAb-anti-AMA-1.1, the above mentioned growth inhibition assay with the huMAb-anti-AMA-1.1 was performed. The recombinant antibody efficiently inhibits the growth of *Plasmodium falciparum* up to 100% (FIG. 7). $IC_{50}$-values were estimated by a nonlinear fitting model using the GraphPad Prism Software package. The results from the standardized samples confirm the reproducibility of the assay in comparison with the European Malaria Reference Repository. The antibody BG98 inhibits the invasion and growth of the malaria parasite by 85-100%. The negative controls (IgG purified from malaria naïve blood donors did not show any inhibitory effect at concentrations up to 6 mg/ml (data not shown). $IC_{50}$-vlaues of the disclosed antibody in the various *P. falciparum* strains are summarized in table 7.

This data confirms the specificity of the huMAb-anti-AMA-1.1. This is the first time that a human recombinant antibody against AMA-1 is presented. It is also shown the first time, that a recombinant human antibody specific for AMA-1 can efficiently inhibit the parasite growth. This confirms the potential of this antibody to be used as a therapeutic or preventive passive vaccine.

Example 6

Synergistic Activity with Other Monoclonalanti-Malarial Antibodies

In order to investigate the potential synergistic inhibitory activity of the antibody huMAb-anti-AMA-1.1, the antibody was tested in combination with the antibody huMAb-anti-MSP10.1 (EP 2 692 357 A1). The antibodies were prepared in a similar way as described in example 5 and the IC50 determined for each antibody alone (example 5 and EP 2 692 357 A1). The synergistic activity was quantified using the checkerboard combination principle. The antibodies huMAb-anti-AMA-1.1 and huMAb-anti-MSP10.1 were mixed in the following ratios in respect to the concentrations of their respective IC50-values: 4 to 1, 2 to 1, 1 to 1, 1 to 2 and 4 to 1. Of each combination, a series of dilution was prepared. The GIA using all these combinations as well as the calculation of the IC50 values was performed similar to example 5. The relative concentration each antibody used in the combination to its individual IC50 concentration used is plotted in the isobologram (FIG. 9). The connection between the IC50 values (=100% on the x and y axis) of the antibodies applied alone represent the line of additivity. Values below the line represent synergistic activity, values above the line represent antagonistic activity. In FIG. 9, it can clearly be seen that the antibodies show a strong synergistic effect.

This data confirms the strong activity of the antibody huMAb-anti-AMA-1.1 and the applicability is strongly enhanced by the potential synergistic activity with antibodies against different epitopes.

TABLE 7

$IC_{50}$-values for the antibody huMAb-anti-AMA-1.1 compared to other well described antibodies of rodent origin

| Antibody | $IC_{50}$ [µg/ml] | 95% Confidence Intervals [µg/ml] |
|---|---|---|
| huMAb-anti-AMA-1.1 | 32 | 31-33 |
| 4G2 (rat) | 106 | 102-110 |
| 1F9 (mouse) | 290 | 272-309 |

TABLE 8

$IC_{50}$-values for the antibody huMAb-anti-AMA-1.1

| P. falciparum strain | $IC_{50}$ [µg/ml] | 95% Confidence Intervals [µg/ml] |
|---|---|---|
| 3D7 | 32 | 31-33 |
| K1 | 113 | 97-131 |
| FCR3 | 230 | 207-255 |
| HB3 | 115 | 101-131 |

Advantageous Embodiments of the Present Disclosure Pertain to isolated human antibodies, or antigen-binding portions thereof, that binds to apical membrane antigen 1 (AMA-1) of *Plasmodium* parasites, in particular to AMA-1 of *Plasmodium falciparum*.

isolated human antibodies, or antigen-binding portions thereof, that binds specific to domain I of AMA-1 of *Plasmodium* parasites, in particular to domain I of AMA-1 of *Plasmodium falciparum* (SEQ ID NO: 16), in particular to domain I of *Plasmodium falciparum* strain 3D7 (Genbank No. U33274), *Plasmodium falciparum* strain FCR-3 (Genbank No. EU586390), *Plasmodium falciparum* strain HB3 (Genbank No. U33277), *Plasmodium falciparum* strain K1 (Genbank No. U33279) or *Plasmodium falciparum* strain Dd2 (Genbank No. DQ218424), wherein the isolated antibodies or antigen-binding portions thereof may inhibit the invasion of the *Plasmodium* parasite into the erythrocyte and/or the growth of the *Plasmodium* parasite within the erythrocyte, in particular inhibits the invasion of various *Plasmodium falciparum* strains, such as the *Plasmodium falciparum* strains 3D7, HB3, FCR-3 and K1.

the isolated antibodies or antigen-binding portions thereof may inhibit the invasion of *Plasmodium* parasite into the erythrocyte and/or the growth of *Plasmodium* parasite within the erythrocyte in a range of 5% to 100%, preferably 10% to 90%, more preferably 20% to 80%, more preferably 30% to 70%, more preferably 40% to 60%.

the isolated antibodies or antigen-binding portions thereof may inhibit the invasion of a *Plasmodium* parasite into the erythrocyte and/or the growth of a *Plasmodium* parasite within the erythrocyte of at least 10%, of at least 20%, of at least 30%, of at least 40%, of at least 50% of at least 60%, in particular of at least 70%, of at least 80%, of at least 90%, of at least 95%, of 100%, the isolated antibodies or antigen-binding portions thereof may be antibodies from human B-cell cultures, recombinant antibodies, synthetic antibodies or antigen-binding portions thereof.

the isolated antibodies or antigen-binding portions thereof may have a light chain variable region (LCVR) and a heavy chain variable region (HCVR) and comprise at least two polypeptides having a sequence selected from SEQ ID NOs 1, 2, 3, 4, 5 and 6, or homologous polypeptides thereof.

In some embodiments, the isolated human antibody or the antigen-binding portion thereof according to the present disclosure has the following characteristics:

a) inhibits the invasion or growth of *Plasmodium* parasites;

b) has a LCVR CDR1 comprising the amino acid sequence of SEQ ID NO: 1; and c) has a HCVR CDR3 comprising the amino acid sequence of SEQ ID NO: 6, and may further has a LCVR CDR2 comprising the amino acid sequence of SEQ ID NO: 2, and a HCVR CDR2 comprising the amino acid sequence of SEQ ID NO: 5, and/or may further has a LCVR CDR3 comprising the amino acid sequence of SEQ ID NO: 3, and a HCVR CDR1 comprising the amino acid sequence of SEQ ID NO: 4.

or a) inhibits the invasion and/or growth of *Plasmodium* parasites;

b) has a LCVR CDR1 comprising the amino acid sequence of SEQ ID NO: 1; and c) has a HCVR CDR2 comprising the amino acid sequence of SEQ ID NO: 5, and may further has a LCVR CDR2 comprising the amino acid sequence of SEQ ID NO: 2, and a HCVR CDR1 comprising the amino acid sequence of SEQ ID NO: 4, and/or may further has a LCVR CDR3 comprising the amino acid sequence of SEQ ID NO: 3, and a HCVR CDR3 comprising the amino acid sequence of SEQ ID NO: 6.

or a) inhibits the invasion and/or growth of *Plasmodium* parasites;

b) has a LCVR CDR1 comprising the amino acid sequence of SEQ ID NO: 1; and c) has a HCVR CDR1 comprising the amino acid sequence of SEQ ID NO: 4, and may further has a LCVR CDR2 comprising the amino acid sequence of SEQ ID NO: 2, and a HCVR CDR2 comprising the amino acid sequence of SEQ ID NO: 5, and/or may further has a LCVR CDR3 comprising the amino acid sequence of SEQ ID NO: 3, and a HCVR CDR3 comprising the amino acid sequence of SEQ ID NO: 6.

or a) inhibits the invasion and/or growth of *Plasmodium* parasites;

b) has a LCVR CDR2 comprising the amino acid sequence of SEQ ID NO: 2; and c) has a HCVR CDR3 comprising the amino acid sequence of SEQ ID NO: 6, and may further has a LCVR CDR1 comprising the amino acid sequence of SEQ ID NO: 1, and a HCVR CDR2 comprising the amino acid sequence of SEQ ID NO: 5, and/or may further has a LCVR CDR3 comprising the amino acid sequence of SEQ ID NO: 3, and a HCVR CDR1 comprising the amino acid sequence of SEQ ID NO: 4.

or a) inhibits the invasion and/or growth of *Plasmodium* parasites;

b) has a LCVR CDR2 comprising the amino acid sequence of SEQ ID NO: 2; and c) has a HCVR CDR2 comprising the amino acid sequence of SEQ ID NO: 5, and may further has a LCVR CDR1 comprising the amino acid sequence of SEQ ID NO: 1, and a HCVR CDR1 comprising the amino acid sequence of SEQ ID NO: 4, and/or may further having a LCVR CDR3 comprising the amino acid sequence of SEQ ID NO: 3, and a HCVR CDR3 comprising the amino acid sequence of SEQ ID NO: 6.

or a) inhibits the invasion and/or growth of *Plasmodium* parasites;

b) has a LCVR CDR2 comprising the amino acid sequence of SEQ ID NO: 2; and c) has a HCVR CDR1 comprising the amino acid sequence of SEQ ID NO: 4, and may further has a LCVR CDR1 comprising the amino acid sequence of SEQ ID NO: 1, and a HCVR CDR2 comprising the amino acid sequence of SEQ ID NO: 5, and/or may further having a LCVR CDR3 comprising the amino acid sequence of SEQ ID NO: 3, and a HCVR CDR3 comprising the amino acid sequence of SEQ ID NO: 6.

or a) inhibits the invasion and/or growth of *Plasmodium* parasites;

b) has a LCVR CDR3 comprising the amino acid sequence of SEQ ID NO: 3; and c) has a HCVR CDR2 comprising the amino acid sequence of SEQ ID NO: 5, and may further has a LCVR CDR1 comprising the amino acid sequence of SEQ ID NO: 1, and a HCVR CDR1 comprising the amino acid sequence of SEQ ID NO: 4, and/or may further has a LCVR CDR2 comprising the amino acid sequence of SEQ ID NO: 2, and a HCVR CDR3 comprising the amino acid sequence of SEQ ID NO: 6.

or a) inhibits the invasion and/or growth of *Plasmodium* parasites;

b) has a LCVR CDR3 comprising the amino acid sequence of SEQ ID NO: 3; and c) has a HCVR CDR1 comprising the amino acid sequence of SEQ ID NO: 4, and may further has a LCVR CDR2 comprising the amino acid sequence of SEQ ID NO: 2, and a HCVR CDR2 comprising the amino acid sequence of SEQ ID NO: 5, and/or may further has a LCVR CDR1 comprising the amino acid sequence of SEQ ID NO: 1, and a HCVR CDR3 comprising the amino acid sequence of SEQ ID NO: 6.

In an isolated human antibody, or antigen-binding portion thereof, according to the present disclosure the LCVR may comprises the amino acid sequences of SEQ ID NOs 1, 2 and 3 and the HCVR may comprises the amino acid sequences of SEQ ID NOs 4, 5 and 6; or a) comprises a heavy chain CDR3 comprising the amino acid sequence of SEQ ID NO: 6, a heavy chain CDR2 comprising the amino acid sequence of SEQ ID NO: 5 and a heavy chain CDR1 comprising the amino acid sequence of SEQ ID NO: 4, or homologous polypeptides or mutants thereof having one or more amino acid substitutions at a contact position or a hypermutation position; and b) comprises a light chain CDR3 comprising the amino acid sequence of SEQ ID NO: 3, a light chain CDR2 comprising the amino acid sequence of SEQ ID NO: 2, and a light chain CDR1 comprising the amino acid sequence of SEQ ID NO: 1, or homologous polypeptides or mutants thereof having one or more amino acid substitutions at a contact position or a hypermutation position, or may has a light chain variable region (LCVR) comprising the polypeptide of SEQ ID NO: 13 and a heavy chain variable region (HCVR) comprising a polypeptide of SEQ ID NO: 14, or homologous polypeptides thereof, in particular the isolated antibody or the antibody fragment thereof comprises a HCVR/LCVR with an amino acid sequence having at least 80 percent sequence identity, in particular 85% percent sequence identity, to either SEQ ID NO: 13 or 14.

The isolated human antibody according to the present disclosure may comprise a heavy chain constant region selected from the group consisting of IgG1, IgG2, IgG3, IgG4, IgM, IgA and IgE constant regions, in particular the antibody heavy chain constant region may be IgG1 or IgG3.

The antigen-binding portion of an isolated human antibody according to the present disclosure may be a Fab fragment or a multimer thereof a F(ab')$_2$ fragment or a multimer thereof a single chain Fv fragment or a multimer thereof.

Furthermore, the present disclosure pertains to:

An isolated nucleic acid molecule, selected from the group consisting of a) a nucleic acid molecule encoding the isolated antibody or antigen-binding portion thereof according to the present disclosure;

b) a nucleic acid molecule encoding for a modified form of the isolated antibody or antigen-binding portion thereof according to the present disclosure, preferably in which one or more amino acid residues are conservatively substituted;

c) a nucleic acid molecule encoding fragments of the isolated antibody or antigen-binding portion thereof according to the present disclosure d) a nucleic acid molecule that is capable of hybridizing to any of the nucleic acid molecules of a)-c) under stringent conditions e) a nucleic acid molecule that is capable of hybridizing to the complement of any of the nucleic acid molecules of a)-d) under stringent conditions f) a nucleic acid molecule having a sequence identity of at least 85% with any of the nucleic acid molecules of a)-e) and encoding for an antibody or antigen-binding portion thereof, g) or a complement of any of the nucleic acid molecules of a)-f).

A vector comprising a nucleotide molecule according to the present disclosure.

A host cell comprising a vector according to the present disclosure.

A composition comprising an antibody or antigen-binding portion thereof according to the present disclosure, wherein the composition is preferably a pharmaceutical and/or diagnostic composition.

A pharmaceutical composition comprising the antibody or an antigen binding portion thereof according to the present disclosure and a pharmaceutically acceptable carrier, wherein The pharmaceutical composition may further comprise an additional agent, in particular a therapeutic agent.

The use of an isolated antibody or antigen-binding portion thereof according to the present disclosure in the prevention and/or treatment of malaria, in particular of malaria tropica.

A purified complex comprising an isolated antibody or antigen-binding portion thereof according to the present disclosure as a specific binding domain and an effector domain, wherein the complex preferably comprises a fusion protein including the binding domain and the effector domain, wherein.

the effector domain may be a toxic substance or a therapeutic agent.

A nucleic acid molecule coding for the complex according to the present disclosure.

A method of producing an isolated antibody or antigen-binding portion thereof according to the present disclosure, wherein the method comprises:

(a) providing a nucleic acid construct comprising a nucleic acid encoding the antibody or antigen-binding portion thereof, (b) introducing the nucleic acid construct into a host cell, and (c) maintaining the host cell under conditions permitting expression of the antibody or antigen-binding portion thereof, wherein the host cell may be a plant cell.

the plant may be selected from the group consisting of algae, moss, monocotyledons and/or dicotyledons.

the plant may be selected from a genus from the group consisting of *Apium, Arabidopsis, Brassica, Capsium, Daucus, Hordeum, Lactuca, Lycopersicon, Nicotiana, Oryza, Petunia, Sinapis, Solanum, Triticum,* wheat or *Zea* the plant may be *Nicotiana benthamiana* or *Nicotiana tabacum.* the antibodies or antigen-binding portions thereof may be isolated and/or purified.

Furthermore, the present disclosure pertains to an isolated human antibody, or antigen-binding portion thereof, that binds to apical membrane antigen 1 (AMA-1) of *Plasmodium* parasites, in particular to AMA-1 of *Plasmodium falciparum*, wherein said antibody or antigen-binding portion thereof inhibits the invasion of a *Plasmodium* parasite into the erythrocyte and/or the growth of the *Plasmodium* parasite within the erythrocyte, in particular wherein the isolated antibody or antigen-binding portion thereof is a monoclonal antibody, an antibody from human B-cell cultures, a recombinant antibody, a synthetic antibody or an antigen-binding portion thereof.

Further embodiments relates to an isolated human antibody, or antigen-binding portion thereof, that binds specific to domain I of AMA-1 (SEQ ID NO: 16) of *Plasmodium falciparum*, wherein said antibody or antigen-binding portion thereof inhibits the invasion of a *Plasmodium falciparum* parasite into the erythrocyte and/or the growth of the *Plasmodium falciparum* parasite within the erythrocyte.

The isolated human antibody according to the present disclosure or the antigen-binding portion thereof may have a light chain variable region (LCVR) comprising a polypeptide having a sequence selected from the group consisting of SEQ ID NO: 1, SEQ ID NO: 2 and SEQ ID NO: 3 and a heavy chain variable region (HCVR) comprising a polypeptide having a sequence selected from the group consisting of SEQ ID NO: 4, SEQ ID NO: 5 and SEQ ID NO: 6, or homologous polypeptides thereof.

Furthermore, in the isolated human antibody according to the present disclosure or the antigen-binding portion thereof, the LCVR may comprise the amino acid sequences of SEQ ID NOs 1, 2 and 3 and the HCVR may comprise the amino acid sequences of SEQ ID NOs 4, 5 and 6, or homologous polypeptides thereof.

Further, the disclosed antibody or the antigen-binding portion thereof may have a light chain variable region (LCVR) comprising the polypeptide of SEQ ID NO: 15 and a heavy chain variable region (HCVR) comprising a polypeptide of SEQ ID NO: 14.

The isolated antibody or the antibody fragment thereof may comprise a HCVR/LCVR comprising an amino acid sequence having at least 80 percent sequence identity, in particular at least 85% percent sequence identity, to either SEQ ID NO: 14 or 13.

According to the present disclosure, the antigen-binding portion may be a Fab fragment, a F(ab')$_2$ fragment, a single chain Fv fragment or multimers thereof.

The present disclosure is further directed to an isolated nucleic acid molecule, selected from the group consisting of a) a nucleic acid molecule encoding the isolated antibody or antigen-binding portion thereof according to the present disclosure;

b) a nucleic acid molecule encoding for a modified form of the isolated antibody or antigen-binding portion thereof according to the present disclosure, preferably in which one or more amino acid residues are conservatively substituted;

c) a nucleic acid molecule that is a fraction, variant, homologue, derivative, or fragment of the nucleic acid molecule presented as SEQ ID NO:7, SEQ ID NO:8, SEQ ID NO:9 SEQ ID NO:10 SEQ ID NO:11 or SEQ ID NO:12;

d) a nucleic acid molecule encoding fragments of the isolated antibody or antigen-binding portion thereof according to the present disclosure, e) a nucleic acid molecule that is capable of hybridizing to any of the nucleic acid molecules of a)-d) under stringent conditions f) a nucleic acid molecule that is capable of hybridizing to the complement of any of the nucleic acid molecules of a)-e) under stringent conditions g) a nucleic acid molecule having a sequence identity of at least 85% with any of the nucleic acid molecules of a)-f) and encoding for an antibody or antigen-binding portion thereof, h) or a complement of any of the nucleic acid molecules of a)-g).

In some advantageous embodiments, the polynucleotide comprises at least two polynucleotides having a sequence selected from the group consisting of SEQ ID NO: 7, SEQ ID NO: 8, SEQ ID NO: 9 SEQ ID NO: 10 SEQ ID NO: 11 and SEQ ID NO: 12 and variants thereof, as permitted by the degeneracy of the genetic code.

Further a vector is disclosed comprising a nucleotide molecule according to the present disclosure and a host cell comprising the vector.

Furthermore, a pharmaceutical composition is disclosed comprising the antibody or an antigen binding portion thereof according to the present disclosure and a pharmaceutically acceptable carrier and the use of the isolated antibody or antigen-binding portion thereof in the prevention and/or treatment of malaria, in particular of malaria tropica.

The genebank numbers of the parasite strains used in the examples are 3D7-U33274, FCR3-EU586390, HB3-U33277, K1-U33279, and DD2-DQ218424.

REFERENCES

The contents of all cited references, including literature references, issued patents, and published patent applications, as cited throughout this application are hereby expressly incorporated by reference.

Altschul, S. F. et al. 1990. "Basic Local Alignment Search Tool." *Journal of Molecular Biology* 215(3):403-10.

Ausubel, F. M. et al. 1989. "Current Protocols in Molecular Biology" *Molecular Reproduction and Development* 1(2): 146-146.

Bird, R. E. et al. 1988. "Single-Chain Antigen-Binding Proteins." *Science* 242(4877):423-26.

Boerner, P., et al. 1991. "Production of Antigen-Specific Human Monoclonal Antibodies from in Vitro-Primed Human Splenocytes." *Journal of Immunology* 147(1):86-95.

Boes, A. et al. 2011. "Affinity Purification of a Framework 1 Engineered Mouse/human Chimeric IgA2 Antibody from Tobacco." *Biotechnology and Bioengineering* 108 (12):2804-14.

Borrmann, S. et al. 2011. "Declining Responsiveness of *Plasmodium falciparum* Infections to Artemisinin-Based Combination Treatments on the Kenyan Coast." *PloS ONE* 6(11):e26005.

Boss, M. A. et al. 1984. "Multichain Polypeptides or Proteins and Processes for Their Production." U.S. Pat. No. 4,816,397 A Brochet, X, et al. 2008. "IMGT/V-QUEST: The Highly Customized and Integrated System for IG and TR Standardized V-J and V-D-J Sequence Analysis." *Nucleic Acids Research* 36 W503-8.

Chothia, C. et al. 1989. "Conformations of Immunoglobulin Hypervariable Regions." *Nature* 342(6252):877-83.

Chothia, C., and A. M. Lesk. 1987. "Canonical Structures for the Hypervariable Regions of Immunoglobulins." *Journal of Molecular Biology* 196(4):901-17.

Dayhoff, M. O. 1979. *Atlas of Protein Sequence and Structure* (Vol 5, Supplement 3). National Biomedical Research.

Durocher, Y. et al. 2002. "High-Level and High-Throughput Recombinant Protein Production by Transient Transfection of Suspension-Growing Human 293-EBNA1 Cells." *Nucleic Acids Research* 30(2):E9.

Fraussen, J. et al. 2010. "A Novel Method for Making Human Monoclonal Antibodies." *Journal of Autoimmunity* 35(2):130-34.

Geysen, H. M. et al. 1984. "Use of Peptide Synthesis to Probe Viral Antigens for Epitopes to a Resolution of a Single Amino Acid." *Proceedings of the National Academy of Sciences of the United States of America* 81(13): 3998-4002.

Harmsen, M. M., De Haard, H. J. 2007. "Properties, production and applications of camelid single-domain antibody fragments." *Applied Microbiology and Biotechnology* 77: 13-22.

Holliger, P. et al. 1993. "'Diabodies': Small Bivalent and Bispecific Antibody Fragments." *Proceedings of the National Academy of Sciences of the United States of America* 90(14):6444-8.

Hoogenboom, H. R., and G. Winter. 1992. "By-Passing Immunisation. Human Antibodies from Synthetic Repertoires of Germline VH Gene Segments Rearranged in Vitro." *Journal of Molecular Biology* 227(2):381-88.

Hu, S. et al. 1996. "Minibody: A Novel Engineered Anti-Carcinoembryonic Antigen Antibody Fragment (single-Chain Fv-CH3) Which Exhibits Rapid, High-Level Targeting of Xenografts." *Cancer research* 56(13):3055-61.

Huston, J. S. et al. 1988. "Protein Engineering of Antibody Binding Sites: Recovery of Specific Activity in an Anti-Digoxin Single-Chain Fv Analogue Produced in *Escherichia coli.*" *Proceedings of the National Academy of Sciences of the United States of America* 85(16):5879-83.

Kabat, E. A. et al. 1992. *Sequences of Proteins of Immunological Interest*. DIANE Publishing.

Kaufman, R. J., and P. A. Sharp. 1982. "Amplification and Expression of Sequences Cotransfected with a Modular Dihydrofolate Reductase Complementary Dna Gene." *Journal of Molecular Biology* 159(4):601-21.

Kipriyanov, S. M. et al. 1995. "Single-Chain Antibody Streptavidin Fusions: Tetrameric Bifunctional scFv-Complexes with Biotin Binding Activity and Enhanced Affinity to Antigen." *Human Antibodies and Hybridomas* 6(3): 93-101.

Kipriyanov, S. M. et al. 1994. "Recombinant Single-Chain Fv Fragments Carrying C-Terminal Cysteine Residues: Production of Bivalent and Biotinylated Miniantibodies." *Molecular immunology* 31(14):1047-58.

Livingstone, C. D., and G. J. Barton. 1993. "Protein Sequence Alignments: A Strategy for the Hierarchical Analysis of Residue Conservation." *Computer Applications in the Biosciences: CABIOS* 9(6):745-56.

Makler, M. T. et al. 1993. "Parasite Lactate Dehydrogenase as an Assay for *Plasmodium falciparum* Drug Sensitivity." *The American Journal of Tropical Medicine and Hygiene* 48(6):739-41.

Martin, A. C. R. 2010. "Protein Sequence and Structure Analysis of Antibody Variable Domains." 33-51 in *Springer Protocols* (*Antibody Engineering, Volume* 2)

McCafferty, J. et al. 1990. "Phage Antibodies: Filamentous Phage Displaying Antibody Variable Domains." *Nature* 348(6301):552-54.

Noedl, H. et al. 2009. "Artemisinin-Resistant Malaria in Asia." *The New England Journal of Medicine* 361 (5): 540-41.

Poljak, R. J. 1994. "Production and Structure of Diabodies." *Structure* 2(12):1121-23.

Reisfeld, R. A. et al. 1985. *Monoclonal Antibodies and Cancer Therapy: Proceedings of the Roche-UCLA Symposium* Held in Park City, Utah, Jan. 26-Feb. 2, 1985.

Reiter, Y. et al. 1996. "Engineering Antibody Fv Fragments for Cancer Detection and Therapy: Disulfide-Stabilized Fv Fragments." *Nature Biotechnology* 14(10):1239-45.

Roestenberg, M. et al. 2008. "Safety and Immunogenicity of a Recombinant *Plasmodium falciparum* AMA1 Malaria Vaccine Adjuvanted with Alhydrogel, Montanide ISA 720 or AS02." *PloS ONE* 3(12):e3960.

Rosenberg, Y. et al. 2013. "Rapid High-Level Production of Functional HIV Broadly Neutralizing Monoclonal Antibodies in Transient Plant Expression Systems." *PloS ONE* 8(3):e58724.

Sambrook, J. et al. 1989. "Molecular Cloning: A Laboratory Manual, Volume 1 to 3, 2nd Edition." in Sambrook J E F Fritsch and T Maniatis *Molecular Cloning A Laboratory Manual Second Edition Vols* 1 2 *and* 3 Cold Spring Harbor Laboratory Press Cold Spring Harbor N.Y. USA *Illus Paper*. Cold Spring Harbor Laboratory Press.

Smith, T. F., and M. S. Waterman. 1981. "Comparison of Biosequences." *Advances in Applied Mathematics* 2(4): 482-89.

Stöcker, M. et al. 2003. "Secretion of Functional Anti-CD30-Angiogenin Immunotoxins into the Supernatant of Transfected 293T-Cells." *Protein Expression and Purification* 28(2):211-19.

Taylor, L. D. et al. 1992. "A Transgenic Mouse That Expresses a Diversity of Human Sequence Heavy and Light Chain Immunoglobulins." *Nucleic Acids Research* 20(23):6287-95.

Taylor, W. R. 1986. "The Classification of Amino Acid Conservation." *Journal of Theoretical Biology* 119(2): 205-18.

Tiller, T. et al. 2008. "Efficient Generation of Monoclonal Antibodies from Single Human B Cells by Single Cell RT-PCR and Expression Vector Cloning." *Journal of Immunological Methods* 329(1-2):112-24.

Urlaub, G., and L. A. Chasin. 1980. "Isolation of Chinese Hamster Cell Mutants Deficient in Dihydrofolate Reductase Activity." *Proceedings of the National Academy of Sciences of the United States of America* 77(7):4216-20.

Ward, E. S. et al. 1989. "Binding Activities of a Repertoire of Single Immunoglobulin Variable Domains Secreted from *Escherichia coli.*" *Nature* 341(6242):544-46.

World Health Organization. 2013. *World Malaria Report* 2013.

What is claimed is:

1. An expression vector comprising a nucleic acid sequence encoding a human antibody or an antigen-binding portion thereof operably linked to a viral regulatory sequence, characterized in that the antibody or antigen-binding portion thereof binds to apical membrane antigen 1 (AMA-1) of a *Plasmodium* parasite, wherein the antibody or antigen-binding portion thereof inhibits invasion of a *Plasmodium* parasite into an erythrocyte and/or growth of the *Plasmodium* parasite within the erythrocyte, wherein the antigen-binding portion of the antibody has a light chain variable region (LCVR) comprising a CDR1 comprising SEQ ID NO:1, a CDR2 comprising SEQ ID NO:2, and a CDR3 comprising SEQ ID NO:3, and a heavy chain variable region (HCVR) comprising a CDR1 comprising SEQ ID NO:4, a CDR2 comprising SEQ ID NO:5, and a CDR3 comprising SEQ ID NO:6.

2. The expression vector according to claim 1, wherein the nucleic acid sequence comprises SEQ ID NO:7, SEQ ID NO:8, SEQ ID NO:9, SEQ ID NO:10, SEQ ID NO:11, and/or SEQ ID NO:12.

3. A host cell comprising the expression vector according to claim 1.

4. A method of producing a human antibody or antigen-binding portion thereof that binds to apical membrane antigen 1 (AMA-1) of a *Plasmodium* parasite, wherein the antibody or antigen-binding portion thereof inhibits invasion of a *Plasmodium* parasite into an erythrocyte and/or growth of the *Plasmodium* parasite within the erythrocyte, wherein the antigen-binding portion of the antibody has a light chain variable region (LCVR) comprising a CDR1 comprising SEQ ID NO:1, a CDR2 comprising SEQ ID NO:2, and a CDR3 comprising SEQ ID NO:3, and a heavy chain variable region (HCVR) comprising a CDR1 comprising SEQ ID NO:4, a CDR2 comprising SEQ ID NO:5, and a CDR3 comprising SEQ ID NO:6, characterized in that the method comprises:

(a) providing a nucleic acid construct comprising a nucleic acid encoding the antibody or antigen-binding portion thereof, (b) introducing the nucleic acid construct into a host cell or adding the nucleic acid construct to a cell-free lysate obtained from eukaryotic or prokaryotic cells, and (c) maintaining the host cell or the cell-free lysate under conditions permitting expression of the antibody or the antigen-binding portion thereof, and optionally (d) isolating and/or purifying and/or processing of the antibody or antigen-binding portion thereof.

5. The method according to claim 4, wherein the host cell is a plant cell, a eukaryotic cell line, or a microorganism.

6. The expression vector of claim 1, wherein the LCVR/HCVR is at least 80% identical to the amino acid sequence of SEQ ID NO: 13 or SEQ ID NO: 14.

7. The expression vector of claim 1, wherein the LCVR comprises SEQ ID NO: 13 and the HCVR comprises SEQ ID NO: 14.

8. The expression vector of claim 1, wherein the antibody or antigen-binding portion thereof binds to AMA-1 of a plurality of different *Plasmodium* parasites, optionally to AMA-1 of a plurality of different *Plasmodium falciparum* parasites including the *P. falciparum* parasite strains 3D7, HB3, FCR3, and K1.

9. The expression vector of claim 1, wherein the antibody or antigen-binding portion thereof is selected from the group consisting of a Fab fragment, a $F(ab')_2$ fragment, a single chain Fv fragment, and a multimer thereof.

10. The method according to claim 5, wherein the plant cell is *Nicotiana benthamiana* or *Nicotiana tabacum*.

11. The method according to claim 5, wherein the eukaryotic cell line is a CHO cell line or a HEK 293 cell line.

12. The method according to claim 5, wherein the microorganism is *Pichia pastoris*.

* * * * *